US012808886B2

(12) United States Patent
Wang et al.

(10) Patent No.: US 12,808,886 B2
(45) Date of Patent: Nov. 24, 2026

(54) DEVICE AND METHODS FOR MEASURING PLATELET-FIBRIN CLOT CONTRACTION KINETICS

(71) Applicant: University of Kentucky Research Foundation, Lexington, KY (US)

(72) Inventors: Qingjun Wang, Lexington, KY (US); Sidney W. Whiteheart, Lexington, KY (US); Ya Luo, Saratoga, FL (US); Kanakanagavalli Shravani Prakhya, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 553 days.

(21) Appl. No.: 18/345,803

(22) Filed: Jun. 30, 2023

(65) Prior Publication Data

US 2024/0044922 A1 Feb. 8, 2024

Related U.S. Application Data

(60) Provisional application No. 63/357,955, filed on Jul. 1, 2022.

(51) Int. Cl.
*G01N 33/86* (2006.01)
*B01L 3/00* (2006.01)

(52) U.S. Cl.
CPC ............ *G01N 33/86* (2013.01); *B01L 3/5023* (2013.01); *B01L 3/502715* (2013.01); *B01L 2200/16* (2013.01); *B01L 2300/0654* (2013.01); *B01L 2300/069* (2013.01); *B01L 2300/0825* (2013.01); *B01L 2300/168* (2013.01)

(58) Field of Classification Search
None
See application file for complete search history.

(56) References Cited

U.S. PATENT DOCUMENTS 9,213,024 B2 12/2015 Sniadecki

FOREIGN PATENT DOCUMENTS

RU 2699050 C1 9/2019

OTHER PUBLICATIONS

Myers, David R; "High Throughput, Multi-Channel, Nano-Mechanical Measurements of Single Platelet Contraction as a Diagnostic Microdevice for Clotting and Bleeding Disorders" Solid-State Sensors, Actuators and Microsystems Workshop, Hilton Head Island, South Carolina, Jun. 8-12, 2014 (Year: 2014).*

Prakhya, Kanakanagavalli Shravani; et al.; "A sensitive and adaptable method to measure platelet-fibrin clot contraction kinetics" Research and Practice in Thrombosis and Haemostatis, 6, e12755, 2022 (Year: 2022).*

* cited by examiner

*Primary Examiner* — David W Berke-Schlessel
(74) *Attorney, Agent, or Firm* — Dinsmore & Shohl LLP

(57) ABSTRACT

This disclosure relates to systems and methods for the observation and/or measurement of clot formation and/or contraction. The system includes reaction chambers arranged with an image capturing device to allow for quantification of clot side-view cross-sectional area over time to determine the kinetics of clot formation and/or contraction. By varying the cellular materials and test agents included in the reaction chambers, it is possible to determine the effect of any particular component may yield on clot contraction. The system provides low-cost set-up, robust software, and multi-sample capacity, thus is a sensitive and flexible system to be used as a "workhorse" tool in a regular laboratory setting for better understanding the molecular features of how platelets mediate clot contraction, with the potential for clinical usages and/or medium throughput laboratory testing and drug screens.

14 Claims, 9 Drawing Sheets

DEVICE AND METHODS FOR MEASURING PLATELET-FIBRIN CLOT CONTRACTION KINETICS

CROSS-REFERENCE TO RELATED APPLICATIONS

This application claims priority to U.S. Provisional Patent Application 63/357,955, filed Jul. 1, 2022, the content of which is hereby incorporated by reference in its entirety.

GOVERNMENT SUPPORT

This invention was made with support from the National Institutes of Health under grants R01HL160910, P20GM12137, P30GM127211, P30DK020579, UL1TR001998 and 1R35HL150818. The government may have certain rights to the invention.

FIELD OF THE INVENTION

This disclosure relates to a device and methods to provide the visualization of clot contraction and measurement of the kinetics of this process.

BACKGROUND

Platelets are small, anucleate, circulating cell fragments that are important for maintaining vascular homeostasis. Vascular disruption activates platelets leading to $\alpha_{IIb}\beta_3$ integrin activation and fibrinogen-binding, linking the extracellular fibrin/fibrinogen network to the platelet actomyosin cytoskeleton, which are important steps in clot formation. Clot contraction is an active squeezing of the clot, reducing its volume and consolidating its mass to form a semi-porous thrombus for preventing blood loss. Platelet-driven clot contraction is important for promoting clot stability and for maintaining blood vessel patency: When contraction is malfunctioning, bleeding can occur (e.g., May Hegglin Anomaly, etc.); alternatively, defective contraction can exacerbate vascular occlusion. During platelet-driven clot contraction, contractile forces generated through ATP hydrolysis by the non-muscle myosin (myosin IIA) are transmitted through the actin cytoskeleton to the fibrin meshwork of a growing clot, resulting in the expulsion of fluid, decrease of clot size, and increase of clot density. Microscopy studies are consistent with this view and show that during initial stages of clot contraction, platelets send out filopodia with longitudinal thin actin filaments that contact and "pull" on fibrin fibers. Despite these general insights, understanding of details of clot contraction at the molecular and cellular level is still limited.

Because clot contraction is integral to platelet function, several assay systems for monitoring clot contraction have been developed. In some assays, clot contraction can be observed in vitro in a test tube using whole blood, platelet-rich plasma (PRP), or washed platelets (with exogenous fibrinogen), and single images of clots at the end of these assays are taken. In other assays, the extent of clot contraction is measured by determining the amount of fluid extruded at a single endpoint. These types of end-point analyses provide little kinetic information and are thus insensitive to subtle alterations during the contraction process. Alternative methods periodically take "snapshots" during the contraction process. The captured images can be roughly quantified using software, such as ImageJ, to approximate contraction rates. However, these methods often employ a limited number of images thus lacking temporal resolution. These types of clot contraction assays yield rather crude and typically qualitative results. Since there is clinical evidence that clot contraction is important in several pathological conditions (e.g., stroke), better resolution of events occurring during clot contraction is needed to more precisely define the cellular and molecular mediators that influence the process, as well as to better assay platelet function for translational and clinical applications.

The recently introduced HemaCore Thrombodynamics Analyzer solves many of the past problems of tracking and quantifying clot contraction. However, despite of its primary use and ease of standardization for evaluating plasma coagulation in clinical samples, especially whole blood, its use in evaluating clot contraction is not standardized. For example, potentially different initiation times of the two samples are not taken into account when using the Analyzer for evaluating clot contraction. Moreover, this instrument suffers from low throughput, monitoring only two samples simultaneously, and thus does not lend itself to common needs for simultaneously monitoring multiple experimental manipulations (e.g., inhibitor/modulator titrations).

SUMMARY

A 1$^{st}$ aspect of the present disclosure, either alone or in combination with any other aspect herein, concerns a device for capturing clot contraction comprising a first strip; at least one reaction chamber housed within the first strip; a light source positioned to provide about equal illumination to all reaction chambers; an aperture between the light source and the at least one reaction chamber to produced diffused light and limit stray light; an image capturing device capable of taking digital or digitizable images and of taking time lapse photos over a time interval, positioned at a fixed distance from the strip; wherein at least one reaction chamber comprises a reaction medium and a reaction mixture, wherein the reaction mixture is comprised of at least two of platelets, calcium, fibrinogen, and thrombin or at least two of platelet rich plasma (PRP), calcium, and thrombin. The reaction chamber may also include an acrylamide plug.

A 2$^{nd}$ aspect of the present disclosure, either alone or in combination with any other aspect herein, concerns the device of the 1$^{st}$ aspect, wherein the first strip is configured to support the reaction chamber and is further configured to provide an unobscured side-view of the reaction chamber.

A3$^{rd}$ aspect of the present disclosure, either alone or in combination with any other aspect herein, concerns the device of the 1$^{st}$ aspect, further comprising a translucent material between the light source and the at least one reaction chamber.

A 4$^{th}$ aspect of the present disclosure, either alone or in combination with any other aspect herein, concerns the device of the 1$^{st}$ aspect, wherein the at least one reaction chamber comprises all four of platelets, calcium, fibrinogen, and thrombin or all three of PRP, calcium, and thrombin.

A 5$^{th}$ aspect of the present disclosure, either alone or in combination with any other aspect herein, concerns the device of the 1$^{st}$ aspect, wherein the at least one reaction chamber comprises all five of platelets, calcium, fibrinogen, non-thrombin agonist (e.g., collagen) and batroxobin or all three of PRP, calcium, and collagen.

A 6$^{th}$ aspect of the present disclosure, either alone or in combination with any other aspect herein, concerns the device of the 1$^{st}$ aspect, wherein the reaction medium comprises a saline solution.

A 7$^{th}$ aspect of the present disclosure, either alone or in combination with any other aspect herein, concerns the device of the 1$^{st}$ aspect, further comprising a test compound.

An 8$^{th}$ aspect of the present disclosure, either alone or in combination with any other aspect herein, concerns the device of the 1$^{st}$ aspect, wherein the first strip is housed in a light impermeable enclosure.

A 9$^{th}$ aspect of the present disclosure, either alone or in combination with any other aspect herein, concerns the device of the 1$^{st}$ aspect, wherein the image capturing device is positioned at the fixed distance from the first strip by an arm operably connected to the strip or a surface underneath the strip.

A 10$^{th}$ aspect of the present disclosure, either alone or in combination with any other aspect herein, concerns the device of the 9$^{th}$ aspect, wherein the arm is adjustable in length and/or height.

An 11$^{th}$ aspect of the present disclosure, either alone or in combination with any other aspect herein, concerns the device of the 1$^{st}$ aspect, further comprising an opaque or translucent material to diffuse the light.

A 12$^{th}$ aspect of the present disclosure, either alone or in combination with any other aspect herein, concerns the device of the 1$^{st}$ aspect, wherein the first strip is curved about the image capturing device.

A 13$^{th}$ aspect of the present disclosure, either alone or in combination with any other aspect herein, concerns the device of the 1$^{st}$ aspect, wherein the first strip is linear.

A 14$^{th}$ aspect of the present disclosure, either alone or in combination with any other aspect herein, concerns the device of the 1$^{st}$ aspect, further comprising a second strip stacked on the first strip.

A 15$^{th}$ aspect of the present disclosure, either alone or in combination with any other aspect herein, concerns the device of the 1$^{st}$ aspect, wherein the one or more reaction chambers are transparent or comprise a transparent window.

A 16$^{th}$ aspect of the present disclosure, either alone or in combination with any other aspect herein, concerns the device of the 1$^{st}$ aspect, wherein the image capturing device is operably connected to a computer or data processing means.

A 17$^{th}$ aspect of the present disclosure, either alone or in combination with any other aspect herein, concerns the device of the 16$^{th}$ aspect, wherein the computer or data processing means is configured to define edges of the clot side-view profile, measure a clot side-view projection area, and/or determine a time point for when clotting is initiated (time 0).

An 18$^{th}$ aspect of the present disclosure, either alone or in combination with any other aspect herein, concerns the device of the 17$^{th}$ aspect, wherein analysis of quantified data is automated.

A 19$^{th}$ aspect of the present disclosure, either alone or in combination with any other aspect herein, concerns a method for quantifying clot contraction comprising: adding a test compound to the reaction medium of the device of the 1$^{st}$ aspect; capturing a series of images with the image capturing device over a time course; determining a time point when clotting initiated; image processing and defining the edges of the clot side-view profile; measuring a clot side-view projection area within the at least one reaction chamber within each of the series of images; and correlating the clot side-view cross-sectional area within each of the series of images to the time course to determine lag time, first derivative of the % clot area-time curve, extent of clot contraction or clot side-view cross-sectional area change, and rates of clot contraction phases.

A 20$^{th}$ aspect of the present disclosure, either alone or in combination with any other aspect herein, concerns a method for collecting clot contraction data, comprising: arranging one or more reaction chambers in a strip configured to support the one or more reaction chambers and to provide a side-view of the reaction chamber; providing illumination to the one or more reaction chambers; providing to the one or more reaction chambers a reaction medium and a reaction mixture, wherein the reaction medium is comprised of at least two of platelets, calcium, fibrinogen, and thrombin or at least two of platelet rich plasma (PRP), calcium, and thrombin; initiating clotting in the one or more reaction chambers at a marked time point; obtaining one or more images of contraction of a clot in the one or more reaction chambers at recorded time points; and processing the one or more images to obtain a value of clot size. The reaction chamber may also include an acrylamide plug.

A 21$^{st}$ aspect of the present disclosure, either alone or in combination with any other aspect herein, concerns the device of the 20$^{th}$ aspect, further comprising assembling the one or more images in chronological order.

A 22$^{nd}$ aspect of the present disclosure, either alone or in combination with any other aspect herein, concerns the device of the 20$^{th}$ aspect, further comprising providing a test compound to the one or more reaction chambers.

A23$^{rd}$ aspect of the present disclosure, either alone or in combination with any other aspect herein, concerns a system for providing information on clot contraction, comprising: a first strip; at least one reaction chamber housed within the first strip; a light source positioned to provide about equal illumination to all reaction chambers; an aperture between the light source and the at least one reaction chamber to produced diffused light and limit stray light; an image capturing device capable of taking digital or digitizable images and of taking time lapse photos over a time interval, positioned at a fixed distance from the strip; and, a computing device operably linked to the image capturing device; wherein at least one reaction chamber comprises a reaction medium and a reaction mixture, wherein the reaction mixture is comprised of at least two of platelets, calcium, fibrinogen, and thrombin or at least two of platelet rich plasma (PRP), calcium, and thrombin; and further wherein the computing device is configured to define edges of the clot side-view profile, measure a clot side-view projection area, and/or determine a time point for when clotting is initiated (time 0). The reaction chamber may also include an acrylamide plug.

BRIEF DESCRIPTION OF THE DRAWINGS

FIG. 2A shows an image of the assay configuration including the digital camera, light box, and samples.

FIG. 2B shows a diagram of the under-sample lighting system.

FIG. 2C shows representative images of resting (R) and thrombin (50-200 mU/mL) stimulated mouse PRP at 0 (upper panel) and 70 min (lower panel) post stimulation during clot contraction.

FIG. 2D shows representative contraction curves from a thrombin titration of clot contraction of mouse PRP in FIG. 2B.

FIG. 2E shows the extent of clot contraction calculated using the system, where extent equals 100×(1−% of Clot Area at 70 min normalized to at 0 min). Mean and SEM for three measurements are plotted. GraphPad Prism and Excel were used for all calculations.

FIG. 3A shows representative contraction curve with green line showing clot area (%) and red line showing the calculated first derivative smoothed with 10 neighbors on each side. The 3 phases of the curve were identified by the maxima ($t_1$) and minima ($t_2$) of the first derivative curve. Lag time was calculated as the time point at which point-to-point area measurements decreased by more than 1%. Extent was the contraction at 100 min ($t_{end}$; normalized to at 0 min). Area under the curve (AUC) was calculated using GraphPad Prism.

FIG. 3B shows a representative dataset recovered from a mouse platelet titration stimulated with thrombin (20 mU/mL, 0.5 mM $CaCl_2$ and 250 μg/mL fibrinogen).

FIG. 3C shows the lag time (min) calculated and plotted versus platelet concentrations. Error bars show SEM for n=2-4; not significant: ns; P≤0.05: *; P≤0.01: ; P≤0.001: * when compared to $5\times10^6$ platelets/mL. Statistical significance was calculated using GraphPad Prism.

FIG. 3D shows the average velocity of contraction (%/min) calculated and plotted versus platelet concentrations. Error bars show SEM for n=2-4; not significant: ns; P≤0.05: *; P≤0.01: ; P≤0.001: * when compared to $5\times10^6$ platelets/mL. Statistical significance was calculated using GraphPad Prism.

FIG. 3E shows the extent of contraction (100×(1−% Area at $t_{end}$)). Error bars show SEM for n=2-4; not significant: ns; P≤0.05: *; P≤0.01: ; P≤0.001: * when compared to $5\times10^6$ platelets/mL. Statistical significance was calculated using GraphPad Prism.

FIG. 3F shows the area under the curve (AUC) calculated and plotted versus platelet concentrations. Error bars show SEM for n=2-4; not significant: ns; P≤0.05: *; P≤0.01: ; P≤0.001: * when compared to $5\times10^6$ platelets/mL. Statistical significance was calculated using GraphPad Prism

FIG. 4A shows the representative contraction curves as determined with a constant concentration ($50\times10^6$/mL) of washed mouse platelets and the indicated concentrations of $CaCl_2$ or 1 mM EGTA. The concentrations of thrombin (20 mU/mL) and fibrinogen (250 μg/mL) were also held constant. Error bars show SEM for n=3; not significant: ns; P≤0.001: *; P≤0.0001: ** when compared to no calcium. Statistical significance was calculated using GraphPad Prism.

FIG. 4B shows lag time (min) as determined with a constant concentration ($50\times10^6$/mL) of washed mouse platelets and the indicated concentrations of $CaCl_2$ or 1 mM EGTA. The concentrations of thrombin (20 mU/mL) and fibrinogen (250 μg/mL) were also held constant. Error bars show SEM for n=3; not significant: ns; P≤0.001: *; P≤0.0001: ** when compared to no calcium. Statistical significance was calculated using GraphPad Prism.

FIG. 4C shows average velocity of contraction (%/min) as determined with a constant concentration ($50\times10^6$/mL) of washed mouse platelets and the indicated concentrations of $CaCl_2$ or 1 mM EGTA. The concentrations of thrombin (20 mU/mL) and fibrinogen (250 μg/mL) were also held constant. Error bars show SEM for n=3; not significant: ns; P≤0.001: *; P≤0.0001: ** when compared to no calcium. Statistical significance was calculated using GraphPad Prism.

FIG. 4D shows extent of clot contraction (100×(1−% Area at $t_{end}$)) as determined with a constant concentration ($50\times10^6$/mL) of washed mouse platelets and the indicated concentrations of $CaCl_2$ or 1 mM EGTA. The concentrations of thrombin (20 mU/mL) and fibrinogen (250 g/mL) were also held constant. Error bars show SEM for n=3; not significant: ns; P≤0.001: *; P≤0.0001: ** when compared to no calcium. Statistical significance was calculated using GraphPad Prism.

FIG. 4E shows AUC (FIG. 4E) as determined with a constant concentration ($50\times10^6$/mL) of washed mouse platelets and the indicated concentrations of $CaCl_2$ or 1 mM EGTA. The concentrations of thrombin (20 mU/mL) and fibrinogen (250 μg/mL) were also held constant. Error bars show SEM for n=3; not significant: ns; P≤0.001: *; P≤0.0001: ** when compared to no calcium. Statistical significance was calculated using GraphPad Prism.

FIG. 5A shows the representative contraction curves as determined with constant concentrations ($50\times10^6$/mL) of washed mouse platelets and the indicated concentrations of thrombin. The concentrations of $CaCl_2$ (0.5 mM) and fibrinogen (250 μg/mL) were also held constant. Error bars show SEM for n=3; P≤0.05: *; P≤0.01: ; P≤0.001: *; P≤0.0001: **** when compared to no thrombin. Statistical significance was calculated using GraphPad Prism.

FIG. 5B shows the lag time (min) as determined with constant concentrations ($50\times10^6$/mL) of washed mouse platelets and the indicated concentrations of thrombin. The concentrations of $CaCl_2$ (0.5 mM) and fibrinogen (250 μg/mL) were also held constant. Error bars show SEM for n=3; P≤0.05: *; P≤0.01: ; P≤0.001: *; P≤0.0001: **** when compared to no thrombin. Statistical significance was calculated using GraphPad Prism.

FIG. 5C shows the average velocity of contraction (%/min) as determined with constant concentrations ($50\times10^6$/mL) of washed mouse platelets and the indicated concentrations of thrombin. The concentrations of $CaCl_2$ (0.5 mM) and fibrinogen (250 μg/mL) were also held constant. Error bars show SEM for n=3; P≤0.05: *; P≤0.01: ; P≤0.001: *; P≤0.0001: **** when compared to no thrombin. Statistical significance was calculated using GraphPad Prism.

FIG. 5D shows the extent of clot contraction (100×(1−% Area at $t_{end}$)) as determined with constant concentrations ($50\times10^6$/mL) of washed mouse platelets and the indicated concentrations of thrombin. The concentrations of $CaCl_2$ (0.5 mM) and fibrinogen (250 μg/mL) were also held constant. Error bars show SEM for n=3; P≤0.05: *; P≤0.01: ; P≤0.001: *; P≤0.0001: **** when compared to no thrombin. Statistical significance was calculated using GraphPad Prism.

FIG. 5E shows the AUC as determined with constant concentrations ($50\times10^6$/mL) of washed mouse platelets and the indicated concentrations of thrombin. The concentrations of $CaCl_2$ (0.5 mM) and fibrinogen (250 μg/mL) were also held constant. Error bars show SEM for n=3; P≤0.05: *; P≤0.01: ; P≤0.001: *; P≤0.0001: **** when compared to no thrombin. Statistical significance was calculated using GraphPad Prism.

FIG. 6A shows the representative contraction curves as determined with constant concentration ($50\times10^6$/mL) of washed mouse platelets and the indicated concentrations of fibrinogen. The concentrations of $CaCl_2$ (0.5 mM) and thrombin (20 mU/mL) were also held constant. Error bars show SEM for n=3-5; P≤0.05: *; P≤0.01: ; P≤0.001: *; P≤0.0001: **** when compared to no fibrinogen. Statistical significance was calculated using GraphPad Prism.

FIG. 6B shows the lag time (min) as determined with constant concentration ($50\times10^6$/mL) of washed mouse platelets and the indicated concentrations of fibrinogen. The concentrations of $CaCl_2$ (0.5 mM) and thrombin (20 mU/mL) were also held constant. Error bars show SEM for n=3-5; P≤0.05: *; P≤0.01: ; P≤0.001: *; P≤0.0001: **** when compared to no fibrinogen. Statistical significance was calculated using GraphPad Prism.

FIG. 6C shows the average velocity of contraction (%/min) as determined with constant concentration ($50\times10^6$/mL) of washed mouse platelets and the indicated concentrations of fibrinogen. The concentrations of $CaCl_2$ (0.5 mM) and thrombin (20 mU/mL) were also held constant. Error bars show SEM for n=3-5; P≤0.05: *; P≤0.01: ; P≤0.001: *; P≤0.0001: **** when compared to no fibrinogen. Statistical significance was calculated using GraphPad Prism.

FIG. 6D shows the extent of clot contraction (100×(1−% Area at $t_{end}$)) as determined with constant concentration ($50\times10^6$/mL) of washed mouse platelets and the indicated concentrations of fibrinogen. The concentrations of $CaCl_2$ (0.5 mM) and thrombin (20 mU/mL) were also held constant. Error bars show SEM for n=3-5; P≤0.05: *; P≤0.01: ; P≤0.001: *; P≤0.0001: **** when compared to no fibrinogen. Statistical significance was calculated using GraphPad Prism.

FIG. 6E shows the AUC as determined with constant concentration ($50\times10^6$/mL) of washed mouse platelets and the indicated concentrations of fibrinogen. The concentrations of $CaCl_2$ (0.5 mM) and thrombin (20 mU/mL) were also held constant. Error bars show SEM for n=3-5; P≤0.05: *; P≤0.01: ; P≤0.001: *; P≤0.0001: **** when compared to no fibrinogen. Statistical significance was calculated using GraphPad Prism.

FIG. 7A shows a representative contraction in the presence of the indicated concentrations of blebbistatin, a selective myosin IIA inhibitor, under standard conditions (20 mU/mL thrombin, 250 μg/mL fibrinogen, 0.5 mM $CaCl_2$, and $50\times10^6$/mL washed mouse platelets).

FIG. 7B shows the lag time (min) calculated and plotted. Error bars show SEM for n=3; not significant: ns; P≤0.05: *; P≤0.01: ; P≤0.001: *; P≤0.0001: **** when compared to no blebbistatin. Statistical significance was calculated using GraphPad Prism.

FIG. 7C shows the average velocity of contraction (%/min) calculated and plotted. Error bars show SEM for n=3; not significant: ns; P≤0.05: *; P≤0.01: ; P≤0.001: *; P≤0.0001: **** when compared to no blebbistatin. Statistical significance was calculated using GraphPad Prism.

FIG. 7D shows the extent of contraction (100×(1−% Area at $t_{end}$)) calculated and plotted. Error bars show SEM for n=3; not significant: ns; P≤0.05: *; P≤0.01: ; P≤0.001: *; P≤0.0001: **** when compared to no blebbistatin. Statistical significance was calculated using GraphPad Prism.

FIG. 7E shows the AUC calculated and plotted. Error bars show SEM for n=3; not significant: ns; P≤0.05: *; P≤0.01: ; P≤0.001: *; P≤0.0001: **** when compared to no blebbistatin. Statistical significance was calculated using GraphPad Prism.

FIG. 8A shows representative contraction in the presence of the indicated concentrations of eptifibatide, a competitive inhibitor of fibrin/fibrinogen binding to $\alpha_{IIb}\beta_3$, under standard conditions (20 mU/mL thrombin, 250 μg/mL fibrinogen, 0.5 mM $CaCl_2$, and $50\times10^6$/mL washed mouse platelets).

FIG. 8B shows the lag time (min) calculated and plotted. Error bars show SEM for n=3; not significant: ns; P≤0.05: *; P≤0.01: ** when compared to no eptifibatide. Statistical significance was calculated using GraphPad Prism.

FIG. 8C shows average velocity of contraction (%/min) calculated and plotted. Error bars show SEM for n=3; not significant: ns; P≤0.05: *; P≤0.01: ** when compared to no eptifibatide. Statistical significance was calculated using GraphPad Prism.

FIG. 8D shows the extent of contraction (100×(1−% Area at $t_{end}$)) calculated and plotted. Error bars show SEM for n=3; not significant: ns; P≤0.05: *; P≤0.01: ** when compared to no eptifibatide. Statistical significance was calculated using GraphPad Prism.

FIG. 8E shows AUC calculated and plotted. Error bars show SEM for n=3; not significant: ns; P≤0.05: *; P≤0.01: ** when compared to no eptifibatide. Statistical significance was calculated using GraphPad Prism.

FIG. 9A shows representative contraction in the presence of the indicated concentrations of 2-deoxyglucose (2DG), an inhibitor of glycolysis (specifically phosphoglucoisomerase), under standard conditions (20 mU/mL thrombin, 250 μg/mL fibrinogen, 0.5 mM $CaCl_2$, and $50\times10^6$/mL washed mouse platelets).

FIG. 9B shows the lag time (min) calculated and plotted. Error bars show SEM for n=3; not significant: ns; P≤0.05: *; P≤0.01: ; P≤0.001: * when compared to no 2DG. Statistical significance was calculated using GraphPad Prism.

FIG. 9C shows average velocity of contraction (%/min) calculated and plotted. Error bars show SEM for n=3; not significant: ns; P≤0.05: *; P≤0.01: ; P≤0.001: * when compared to no 2DG. Statistical significance was calculated using GraphPad Prism.

FIG. 9D shows extent of contraction (100×(1−% Area at $t_{end}$)) calculated and plotted. Error bars show SEM for n=3; not significant: ns; P≤0.05: *; P≤0.01: ; P≤0.001: * when compared to no 2DG. Statistical significance was calculated using GraphPad Prism.

FIG. 9E shows AUC calculated and plotted. Error bars show SEM for n=3; not significant: ns; P≤0.05: *; P≤0.01: ; P≤0.001: * when compared to no 2DG. Statistical significance was calculated using GraphPad Prism.

FIG. 10 shows a remote computing device for measuring platelet-fibrin clot contraction kinetics.

DETAILED DESCRIPTION

Figure 1:
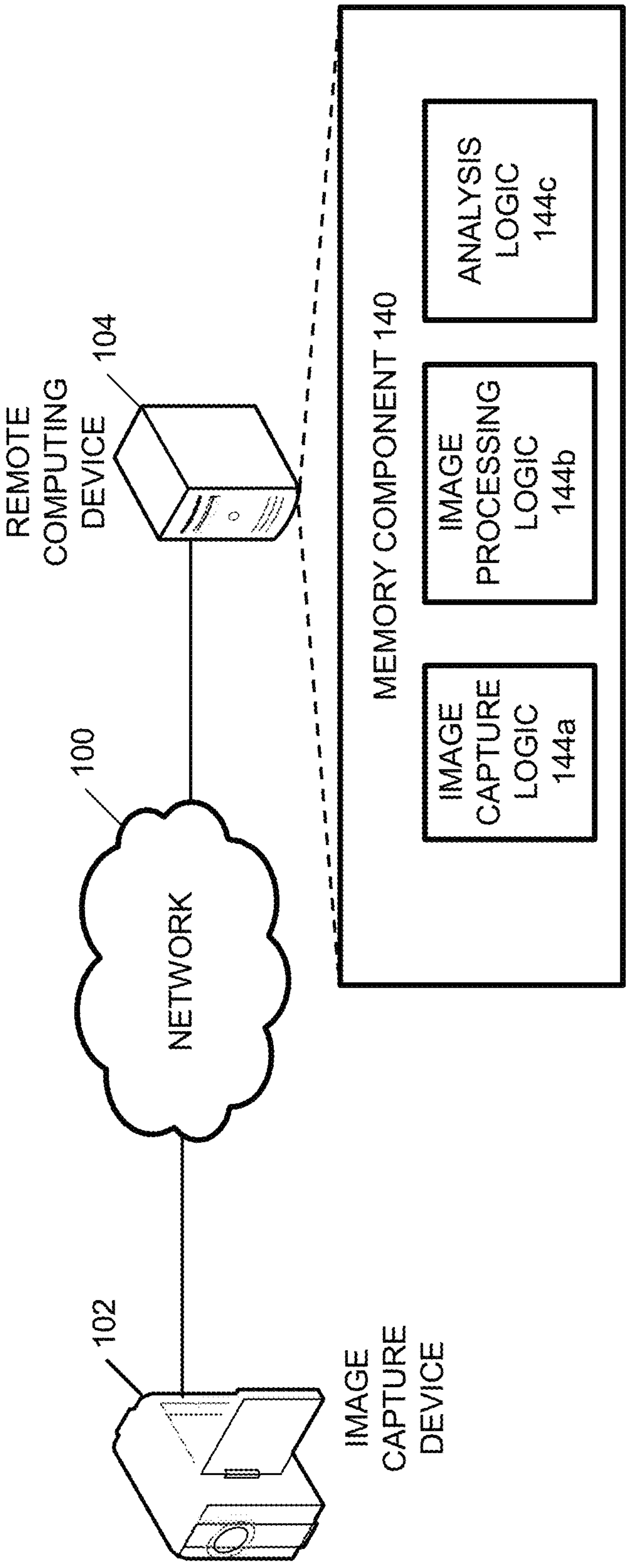
FIG. 1 shows an overview of a computing environment for measuring platelet-fibrin clot contraction kinetics.

This disclosure relates to a device and methods of using the system for tracking and quantifying clot contraction. In some aspects, the present disclosure provides a device or system that can successfully capture clot contraction with a coupled single standard digital camera and operable timer thereof. In some aspects, the device and system allow for the capture and assessment of multiple samples each with potentially different initiation times for clot formation and contraction. In some aspects, the present disclosure concerns the development of the system and accompanying software to automate processing of collected clot images to provide clot tracking and quantification. As set forth herein, the device and system provide for detection of the three key phases of clot contraction and demonstrated the expected dependence of clot contraction on platelet number, calcium, an agonist (e.g. thrombin), fibrinogen, myosin IIA, fibrin-integrin interaction, and glycolysis.

Clot Observing Device

In some aspects, the present disclosure concerns a device or system that allows for methods of capturing and/or measuring clot contraction. In some aspects, the device or system includes a strip configured (or other similar configuration such as tube-by-tube rather than a whole strip) to allow bottom-to-up (or other directions, such as from the side or top) illumination of transparent reaction chambers therein. By arranging the reaction chambers in a fashion whereby one or more cameras can capture an unobstructed side-view, the one or more cameras can monitor the profile and/or obtain images from all reaction chambers simultaneously. In some aspects, a single camera may be sufficient. In some aspects, the strip may be linear (straight or curved). It will be appreciated in the art that the number of reaction chambers can in some aspects be limited by the field of view of the camera monitoring and/or capturing images, as well as the distance of the camera from the device. It will also be appreciated, that more than one camera may be utilized. In aspects where a digital image is captured, it will be appreciated that increasing the distance between the camera and the reaction chambers may reduce the number of pixels available to capture the clot or a portion thereof and accordingly may in some aspects reduce the accuracy. It may also be appreciated that in some aspects, a user may not be able to initiate reactions in each reaction chamber at the same instant or thereabout. As such, the number of reaction chambers in the strip may be limited by user capabilities. In other aspects, a user or a visual trigger (such as placing the reaction chamber in place) can mark the initiation of a clotting reaction within each reaction chamber (or "time zero") through the camera and accordingly record and/or monitor and/or measure the reactions in each chamber independently. In some aspects, an arm may be used to retain or steady the camera. It will be appreciated that the introduction of an arm allows for a constant distance from the reaction chamber(s), as well as a constant height and/or perspective of each reaction chamber. In some aspects, the arm is adjustable, allowing a user to adjust the distance and/or height of the camera. In some aspects, the arm can be moveable, such as through rotation about a fixed point by anchoring a distal end of the arm.

In some aspects, the strip is configured to house the reaction chambers. It will be appreciated that in some aspects, it may be possible for the reaction chambers to be free standing and as such, the strip need no particular configuration but may still serve to provide a linear (straight or curved) line upon which each reaction chamber may be centered to ensure similar or equidistance from the image capturing device. It will be appreciated that calculating percentage of clot area change within each sample allows for variance in distance to be effectively cancelled. In other aspects, a reaction chamber may not remain still or balanced in a still position without assistance, for example, a round bottomed cylinder. In such instances, the linear strip may include at least two strips maintained in a parallel or near parallel and horizontal arrangement with the upper strip configured with an aperture to receive passage of the reaction chamber and allow the reaction chamber to rest on the lower strip, such that the walls of the aperture provide support for the walls of the reaction chamber. For example, in instances where the reaction chamber is a round bottomed cylinder, the aperture of the upper strip may feature circular apertures of a slightly larger circumferences such that the reaction chambers can pass through and rest on the bottom strip while maintain upright position. In some instances, it may be of benefit to shape the lower strip to receive the reaction chamber. For example, in stances where the reaction chamber is a round bottomed tube, a concave or recessed area within the lower strip may help to secure the reaction chamber. It will be appreciated that in some instances the lower strip may be replaced by a surface provided by other aspects of the device or system, such as a table surface or an exterior surface of an underlying light source, once the reaction chambers are in place for measuring and/or detecting clot formation and/or contraction.

In some aspects, the device or system of the present disclosure concerns arrangements to provide illumination to the reaction chambers as set forth herein. As described herein, the reaction chambers house solutions wherein monitoring for clot formation and/or contraction occurs by a single camera focused on the profile thereof, wherein the camera collects images that allow for clot side-view projection area measurement over a time course. It will be appreciated that in some aspects, the clot, while possessing a three-dimension shape, can be measured by the visible area when viewed in profile from the side. In some aspects, the collected images may allow for the measurement and/or observation of clot contraction. In some aspects, the collected images may be put together as a film to observe the process over time.

In some aspects, the present disclosure concerns providing a linear (straight or curved) array or strip of reaction chambers to an image capturing device so that profile images of clot in each reaction chamber can be captured and calculations of clot side-view projection area and/or rate of change can be therefrom obtained. In some aspects, the array or strip provides a linear array of reaction chambers. In some aspects the reaction chambers may be in two or more stacked layers along the strip. In some aspects, the reaction chamber is of a transparent material to allow for accurate image capture of the progress of clot formation and/or contraction therein. In some aspects, the reaction chamber may be of a transparent glass or plastic. It will be appreciated that the reaction chambers may be of any suitable size or shape or material, provided that the system be arranged such that clot formation and/or contraction can be adequately imaged. In further aspects, it is of potential benefit that the reaction chamber material be inert or non-reactive with any component of the samples to be tested in the reaction chambers. In some aspects, the reaction chambers may be a glass tube or cuvette or a siliconized glass tube or cuvette. In some aspects, the tube or cuvette may be of a transparent polymer, such as polyethylene.

In some aspects, the present disclosure concerns providing a reaction medium for clot formation and/or contraction to occur in, such as a reaction medium within each reaction chamber. In some aspects, the reaction medium may be a cell culture medium or a medium derived therefrom. Examples of cell culture media include HEPES (4-(2-hydroxyethyl)-1-piperazineethanesulfonic acid), MEM (minimal essential medium), HEPES-Tyrode buffer, platelet additive solutions (PAS), HEPES, DMEM (Dulbecco's modified Eagle's media), DMEM/F12, GMEM (Glasgow minimal essential medium), PBS (phosphor buffered saline), DPBS (Dulbecco's PPBS), HBSS (Hank's balanced salt solution), EBSS (Earle's balanced salt solution), RPMI (Roswell Park Memorial Institute), Grace's Insect Media, and IMDM (Iscove's modified Dulbecco's medium). Reaction may further include an antibiotic, additional salts, amino acids, vitamins, serum (such as fetal bovine serum), buffers, carbohydrates, proteins, peptides, fatty acids, lipids, acetate, citrate, phosphate, potassium, magnesium, glucose, sodium bicarbonate, calcium, sodium, chloride, and/or trace elements. In some aspects, the reaction medium may include fluid from a subject, such as whole blood or a medium derived therefrom, such as plasma.

In further aspects, each reaction chamber may include an acrylamide plug or pad at the base. In some aspects, the reaction chambers can be initially cleaned with distilled water followed by 95% ethanol, air dried, and then a polyacrylamide solution is transferred to the bottom of the reaction chamber and optionally covered with distilled water to allow for even polymerization. In some aspects, the polyacrylamide solutions may be sufficient for gel of about 5% to about 20% acrylamide polymer, including 6, 7, 8, 9, 10, 11, 12, 13, 14, 15, 16, 17, 18, and 19% acrylamide. In some aspects, the acrylamide of prepared as a solution with an initiator, such as ammonium persulfate and/or TEMED (tetramethylethylenediamine), added just before transferring to reaction chambers. Following polymerization, each reaction chamber and/or acrylamide plug may be washed or rinsed with the reaction medium to be used.

In some aspects, each reaction chamber may be provided with one or more cellular materials needed for clot formation and/or contraction. It will be appreciated that the core requirements for each component for clot formation and/or contraction may be varied depending on what aspect may be assessed by the user. As identified herein, there are four minimum cellular material requirements for clot formation and/or contraction of washed platelets, including platelets, calcium, fibrinogen and thrombin. There are only three minimum cellular material requirements for clot formation and/or contraction of PRP, including PRP, calcium, and thrombin. In some aspects, it may be desirable for the user to determine the dynamic effects of the presence of one component at varying concentrations on clot formation and/or contraction while maintaining the remaining components at constant concentrations. In other aspects, it may be desirable for the user to utilize a selected set of concentrations of all four components to assess the ability of a fifth or test compound to affect, positively or negatively, clot formation and/or contraction. In further aspects, it may be desirable to test two or more test compounds. In other aspects, it may be desirable to test whether a test compound(s) can functionally replace calcium and/or a platelet and/or thrombin and/or fibrinogen in clot formation and/or contraction. In further aspects, it may be desirable to test the ability of a mutation in fibrinogen, thrombin, and/or other protein to affect clot formation and/or contraction. In other aspects, it may be desirable to test if an abnormal or modified platelet affects clot formation and/or contraction. For example, as set forth herein, blebbistatin, eptifibatide and 2DG can be added to assess the roles of myosin IIA, fibrin-integrin interaction, and glucose metabolism, respectively. In some aspects, the reaction chamber may include further clot formation and/or contraction contributors, such as red blood cells.

In some aspects, it may be desirable to provide or store the cellular materials in a medium that inhibits or reduces the platelet aggregation and clot initiation, such as with the presence of apyrase in a PRP or platelet solution. Such inhibitors may be washed off by gently bringing down platelets and re-suspending them in an inhibitor-free medium prior to bringing together cellular material requirements or dispensing to the reaction chamber.

In other aspects, the present disclosure concerns providing light to the reaction chamber to sufficiently illuminate clot formation and/or contraction therein for accurate image capture, processing, and/or measurement. In some aspects, the light source is positioned to provide equal or near equal illumination to each reaction chamber. In some aspects, the lighting of the reaction chamber may be of a diffuse or ambient nature such that a direct source of light or direct sources of light do not cause reflections or provide a distortion of the clot formation and/or contraction images. In some aspects, the system can be placed in a dark room or a dark chamber to control the amount and/or direction of light that illuminates the reaction chamber(s). In further aspects, dark or opaque materials can be introduced within the chamber to further control light. In some aspects, the light may be provided to the reaction chambers by positioning a light source, such as an LED, a light bulb or a light box, behind an aperture to direct the light. The aperture may be of individual apertures at each reaction chamber or a linear (straight/curved) aperture along the length of the linear (straight/curved) arrangement of the reaction chambers. In some aspects, the aperture may be beneath the reaction chamber. In other aspects, the aperture may be above the reaction chamber. In further aspects, the aperture may be along the profile or side of the reaction chamber. In even further aspects, the aperture may be at multiple positions around the reaction chamber.

In some aspects, the light passing through the aperture is diffused by first passing through a translucent or diffusing material, such as a tissue paper, a parchment paper, ground glass, Teflon, opal glass and/or greyed glass. It will be appreciated that the diffuser need not be of a particular material, but instead of a suitable level of translucence. Accordingly, the diffuser may be of a plastic, acrylic, fabric, or gel. In some aspects, due to heat energy from the light, the ability of the diffuser to withstand such may be an additional consideration.

In some aspects, the device or parts thereof may be enclosed in a light impermeable enclosure. In some aspects, the linear strip and/or reaction chambers are housed within the light impermeable enclosure. In some aspects, the image capturing device may be housed within the light impermeable enclosure. In other aspects, the light source may be housed either inside or outside the light impermeable enclosure. It will be apparent that with the light source housed outside the light impermeable enclosure, the enclosure may include an aperture to provide illumination to the reaction chambers. In some aspects, the translucent or diffusing material may cover the aperture to diffuse light as it enters the light impermeable enclosure. In further aspects, the device may include a dark or contrasting material positioned to provide a contrasting background for the image capturing device behind the reaction chambers and/or to the sides of the reaction chambers (as viewed from the image capturing device).

In some aspects of the present disclosure, an image capture device is positioned to capture images, such as a profile image, of the reaction chambers. In further aspects, the image capturing device is positioned at a stationary point from the reaction chambers such that repeated images can be captured over a time course while the captured image does not fluctuate in perspective size or position between images. In some aspects, the image capturing device may be maintained at a constant distance from the reaction chambers through the use of a fixed arm connected, directly or indirectly, to both the linear strip and the image capturing device. In further aspects, using an image capturing device that captures a digital image may improve accuracy of calculation of clot side-view projection area.

In further aspects, the image capturing device may be configured to capture as complete an image of a forming and/or contracting clot. In further aspects, the image capturing device may be configured to capture complete repeated images of the forming and/or contracting clot. In some aspects, the image capturing device may be configured by f-stop or aperture size, lens selection, and/or exposure time. In some aspects, capturing a large and/or highly pixelated image is of benefit for accurate measurement of the clot side-view projection area. Such may be enhanced by use of a macro lens, an appropriate f-stop or aperture size, and/or a high pixel resolution.

Clot Measurement

In some aspects, the present disclosure concerns processing of images or collected images to determine the clot size (specifically, side-view projection area) of a clot at any given time point during formation and/or contraction. In further aspects, the rate of formation and/contraction of the clot may be determined based on change in size over a selected time period.

Referring now to the drawings, FIG. 1 shows a computing environment for measuring platelet-fibrin clot contraction kinetics. As illustrated, the computing environment may include a network 100, which may include a wide area network (wired or wireless), such as the internet, a cellular network, or other communications network for communicating devices across a wide area. Similarly, the network 100 may include a wired or wireless local area network for communicating data, including tone-based and/or other peer-to-peer network communications, as described herein.

Coupled to the network 100 are an image capture device 102 and a remote computing device 104. The image capture device 102 may be configured as still image camera, a video camera, an SLR camera, an infrared camera, a heat sensing camera, a mobile device, personal computer, and/or other device that is configured to capture images as described herein.

The remote computing device 104 may be configured as and/or include a personal computer, tablet, mobile device, server, and/or other device for providing processing options of the imagery captured by the image capture device 102. As an example, the image capture device 102 may be configured to capture images and send those images to the remote computing device 104, which may process the images and provide the data depicted in FIGS. 2C-9E and described herein.

The remote computing device 104 may thus include a memory component 140, which may store image capture logic 144*a*, image processing logic 144*b*, and analysis logic 144*c*. As discussed in more detail below, the image capture logic 144*a* may cause the remote computing device 104 to trigger the image capture device 102 to capture one or more images and/or receive imagery from the image capture device. The image processing logic 144*b* may be configured for causing the remote computing device 104 to process raw and/or cropped imagery as inputs and clot area (e.g., in units of pixel size) as outputs, as well as perform any post image processing. The analysis logic 144*c* may cause the remote computing device 104 to perform further analysis of the clot side-view projection area and/or perform other functionality provided herein.

Images obtained by the image capture device 102 are analyzed by the remote computing device 104 via the analysis logic 144*c* to determine the boundaries of the side-view projection of a clot present and then provide a clot area value. The percent clot areas at given time points ($Y_t$) are then obtained by dividing measured clot area values by the area of unstimulated platelet-containing reaction mixture measured at time zero, then multiplied by 100. FIGS. 2C-2E demonstrate changes in clot contraction in the obtained images at two different time points (0 min and 70 min). Image data were analyzed computationally (using GraphPad and Excel) to determine the lag time (initial time at which the point-to-point change in clot area exceeds 1%); area under the curve (calculated with GraphPad); clot contraction extent (relative clot size at a defined endpoint, i.e., 100 min) and average velocity (average of the first derivative of the smoothed clot area curve over the entire time course; see the red curve in FIG. 3A, calculated with GraphPad Prism 8.4.3). To better understand different stages of clot contraction, a piece-wise analysis was carried out by dividing the curve into 3 phases based on a plot of the curve's first derivative (FIG. 3A). As was previously shown by Tutwiler et al. (Blood 127(1): 149-159, 2016, doi.org/10.1182/blood-2015-05-647560), using this piece-wise analysis allows for the calculation of rates and clot contraction % for each phase of the process. The transition times for phases 1-to-2 and 2-to-3, $t_1$ and $t_2$, were determined from the local maxima and minima of the first derivatives of the smoothened clot area curves. The size of the smoothening window was determined based on the time resolution of the raw data and the kinetics of the process. We chose to smoothen with 10 neighbors on each side. The initial or initiation phase ($t_0$-$t_1$) was fit to an exponential equation; the second or contraction phase ($t_1$-$t_2$) was fit to a linear equation; and the third or stabilization phase ($t_2$-$t_{end}$) was fit to an exponential equation, and the rates ($k_1$, $k_2$, and $k_3$) for each phase of the contraction curve were calculated using available software and the following equations.

Initiation Phase $t_0<t<t_1\ y=y_0-(y_0-y_1)(1-e^{-k_1t})$ Phase 1:

Contraction Phase $t_1<t<t_2\ y=y_1-k_2t$ Phase 2:

Stabilization Phase $t_2<t<t_{end}\ y=y_2-(y_2-y_3)(1-e^{-k_3t})$ Phase 3:

Statistical significance was assessed using one-way ANOVA (Analysis of Variance) followed by a multiple comparison test with the Bonferroni method.

Figure 2A:
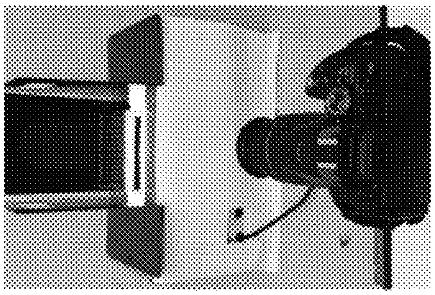
FIGS. 2A-E shows assay configuration and examples of data.
Figure 2B:
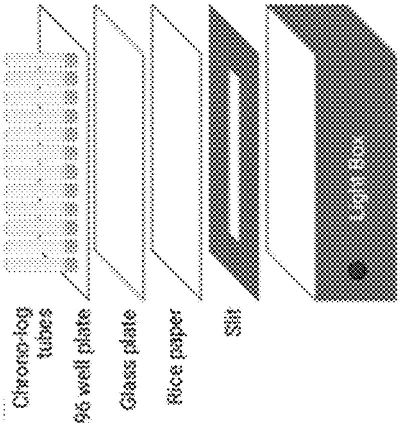
Figure 2C:
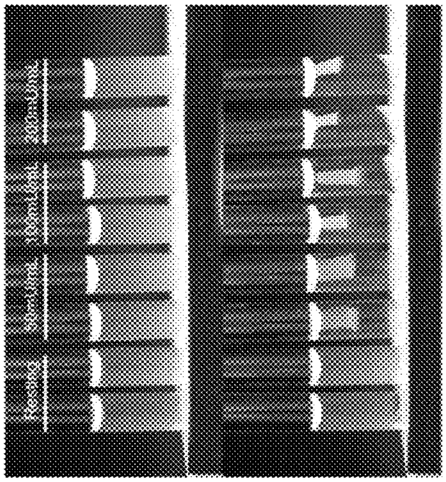
Figure 2D:
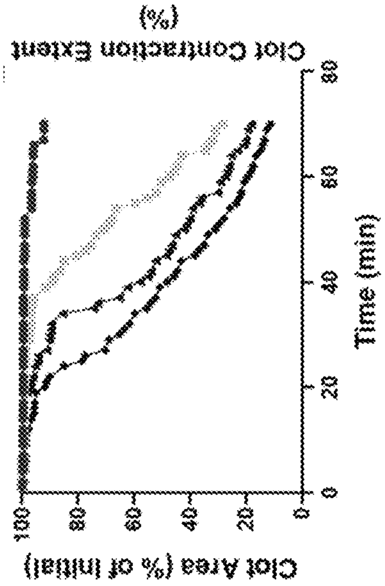
Figure 2E:
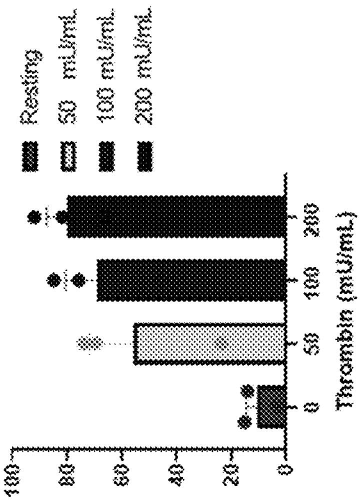
Figure 3A:
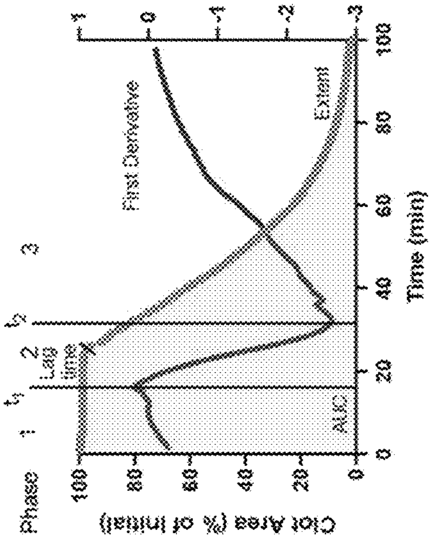
FIGS. 3A-F show analysis of clot contraction: platelet dependence.
Figure 3B:
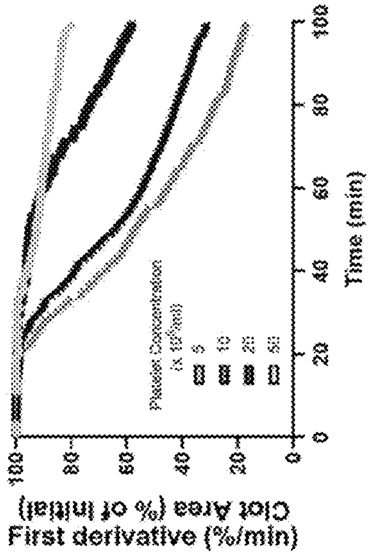
Figure 3C:
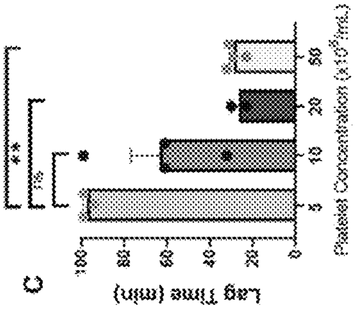
Figure 3D:
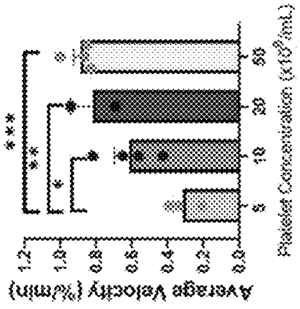
Figure 3E:
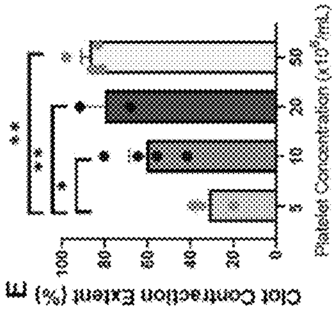

FIGS. 2A-E shows assay configuration and examples of data. FIG. 2A shows an image of the assay configuration including the digital camera, light box, and samples. FIG. 2B shows a diagram of the under-sample lighting system. FIG. 2C shows representative images at 0 (upper panel) and 70 min (lower panel) of clot contraction in resting (R) and thrombin (50-200 mU/mL) stimulated mouse PRP. FIG. 2D shows representative contraction curves from a thrombin titration of clot contraction of mouse PRP in FIG. 2C. FIG. 2E shows the extent of clot contraction calculated using the system, where extent equals 100×(1−% of Clot Area at 70 min normalized to at 0 min). Mean and standard error of the mean (SEM) for three measurements are plotted. GraphPad Prism and Excel were used for all calculations, FIGS. 3A-F show analysis of clot contraction: platelet dependence. FIG. 3A shows a representative contraction curve with green trace showing clot area (%) and red trace showing the calculated first derivative smoothed with 10 neighbors on each side. The 3 phases of the curve were identified by the local maxima ($t_1$) and minima ($t_2$) of the first derivative curve. Lag time was calculated as the time point at which point-to-point area measurements decreased by more than 1%. Extent was the contraction at 100 min ($t_{end}$; normalized to at 0 min). Area under the curve (AUC) was calculated using GraphPad Prism. FIG. 3B shows a representative dataset recovered from a mouse platelet titration stimulated with thrombin (20 mU/mL, 0.5 mM $CaCl_2$ and 250 μg/mL fibrinogen). The lag time (min; FIG. 3C), average velocity (%/min; FIG. 3D), extent of contraction (100×(1−% Area at $t_{end}$); FIG. 3E), and AUC (FIG. 3F) were calculated and plotted versus platelet concentrations. Error bars show SEM for n=2-4; not significant: ns; P≤0.05: *; P≤0.01: ; P≤0.001: * when compared to $5\times10^6$ platelets/mL. Statistical significance was calculated using GraphPad Prism.

Figure 4A:
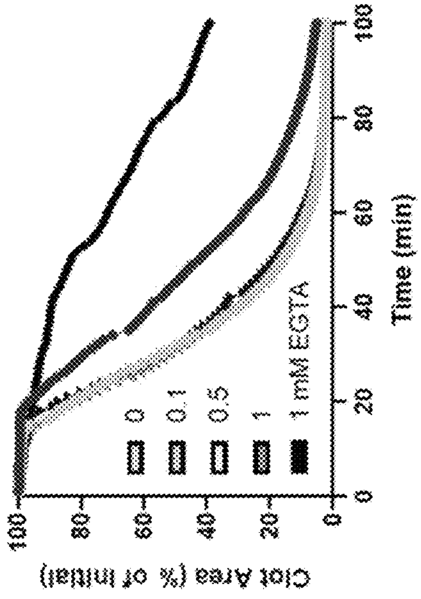
FIGS. 4A-E show analysis of clot contraction: calcium dependence.
Figure 4B:
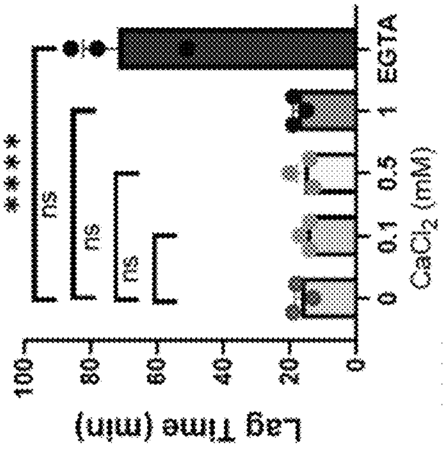
Figure 4C:
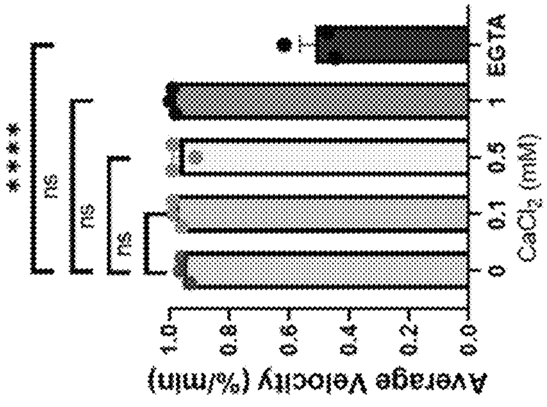
Figure 4D:
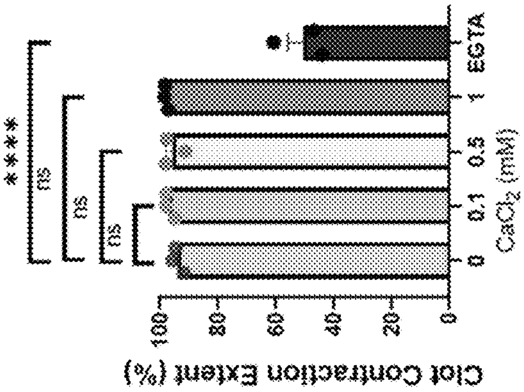
Figure 4E:
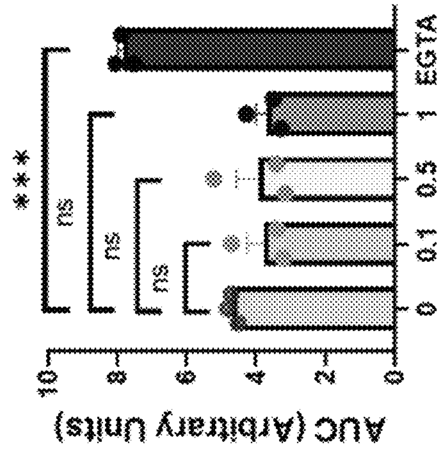

FIGS. 4A-H show analysis of clot contraction: calcium dependence. Shown are the representative contraction curves (FIG. 4A), lag time (min; FIG. 4B), average velocity (%/min; FIG. 4C), extent of clot contraction (100×(1−% Area at $t_{end}$); FIG. 4D), and AUC (FIG. 4E) as determined with a constant concentration of washed platelets ($50\times10^6$/mL mouse platelets) and the indicated concentrations of $CaCl_2$ or 1 mM EGTA. The concentrations of thrombin (20 mU/mL) and fibrinogen (250 μg/mL) were also held constant. Error bars show SEM for n=3; not significant: ns; P≤0.001: *; P≤0.0001: ** when compared to no calcium. Statistical significance was calculated using GraphPad Prism.

Figures 5A, 5B, 5C, 5D, 5E:
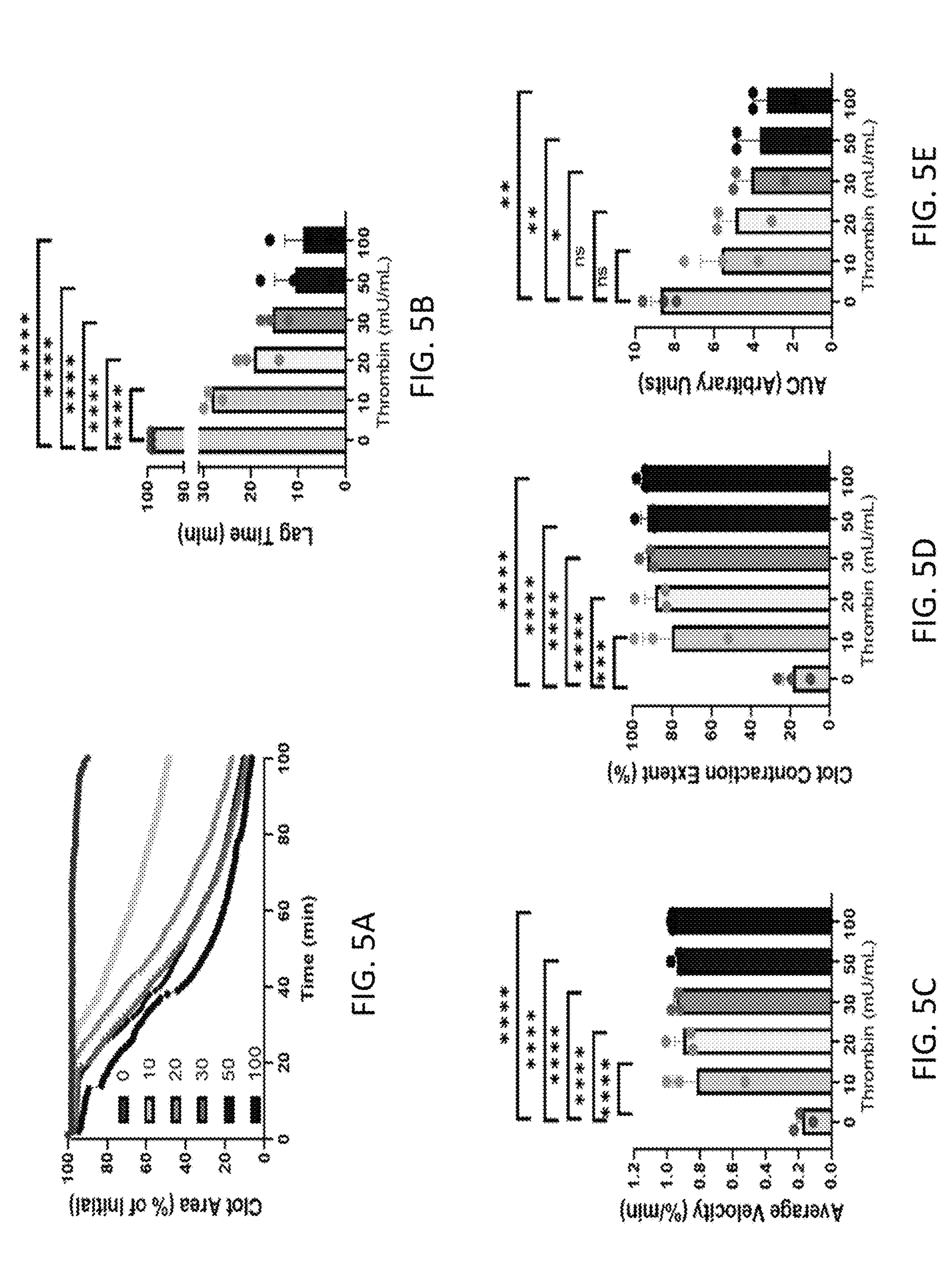
FIGS. 5A-E show analysis of clot contraction: thrombin dependence.

FIGS. 5A-E show analysis of clot contraction: thrombin dependence. Shown are the representative contraction curves (FIG. 5A), lag time (min; FIG. 5B), average velocity (%/min; FIG. 5C), extent of clot contraction (100×(1−% Area at $t_{end}$); FIG. 5D), and AUC (FIG. 5E) as determined with constant concentrations of washed platelets ($50\times10^6$/mL mouse platelets) and the indicated concentrations of thrombin. The concentrations of $CaCl_2$ (0.5 mM) and fibrinogen (250 μg/mL) were also held constant. Error bars show SEM for n=3; P≤0.05: *; P≤0.01: ; P≤0.001: *; P≤0.0001: **** when compared to no thrombin. Statistical significance was calculated using GraphPad Prism.

Figure 6A:
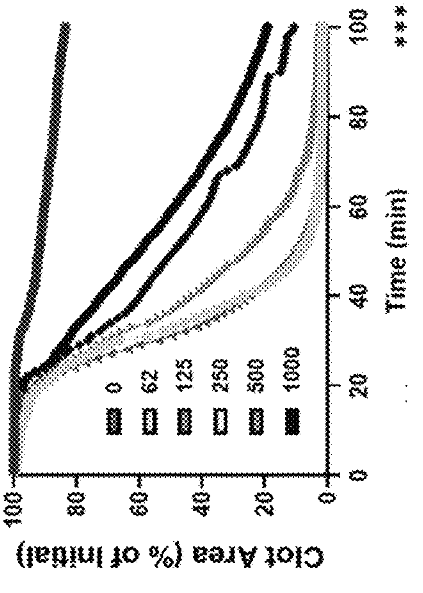
FIGS. 6A-E show analysis of clot contraction: fibrinogen dependence.
Figure 6B:
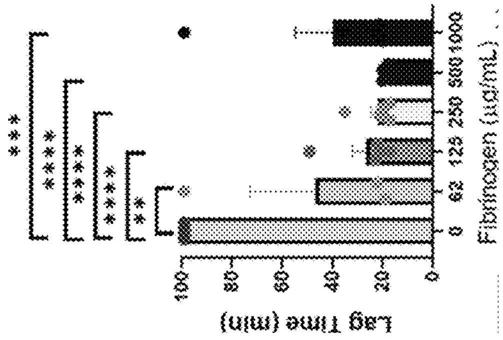
Figure 6C:
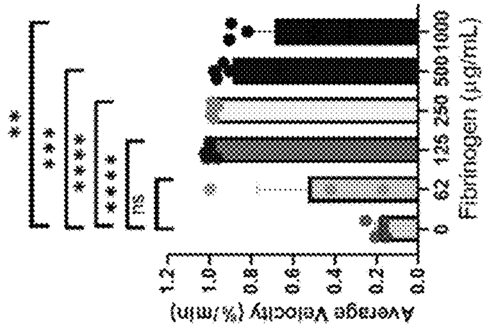
Figure 6D:
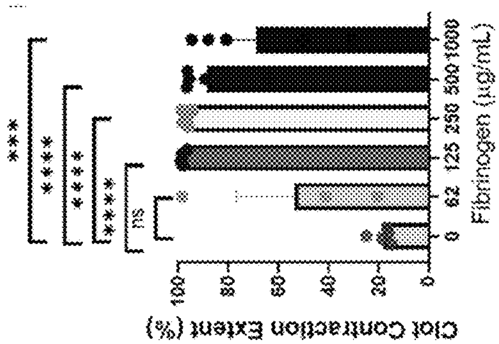
Figure 6E:
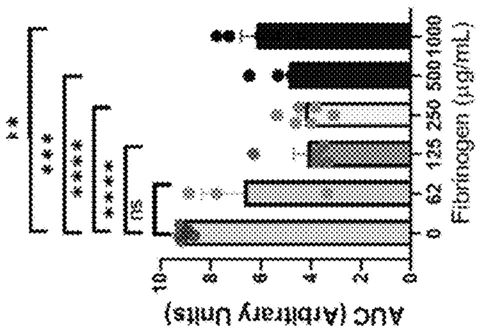

FIGS. 6A-E show analysis of clot contraction: fibrinogen dependence. Shown are the representative contraction curves (FIG. 6A), lag time (min; FIG. 6B), average velocity (%/min; FIG. 6C), extent of clot contraction (100×(1−% Area at $t_{end}$); FIG. 6D), and AUC (FIG. 6E) as determined with constant concentration of washed platelets ($50\times10^6$/mL mouse platelets) and the indicated concentrations of fibrinogen. The concentrations of $CaCl_2$ (0.5 mM) and thrombin (20 mU/mL) were also held constant. Error bars show SEM for n=3-5; P≤0.05: *; P≤0.01: ; P≤0.001: *; P≤0.0001: **** when compared to no fibrinogen. Statistical significance was calculated using GraphPad Prism.

Figure 7A:
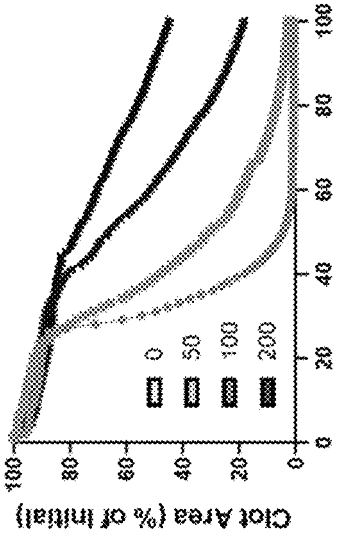
FIGS. 7A-E show the role of Myosin IIA in clot contraction.
Figure 7B:
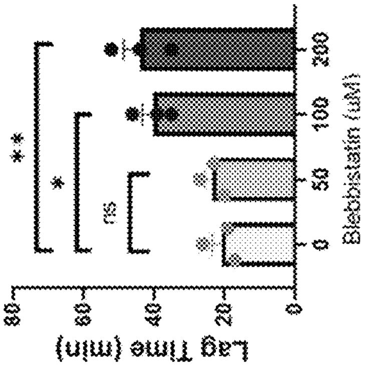
Figure 7C:
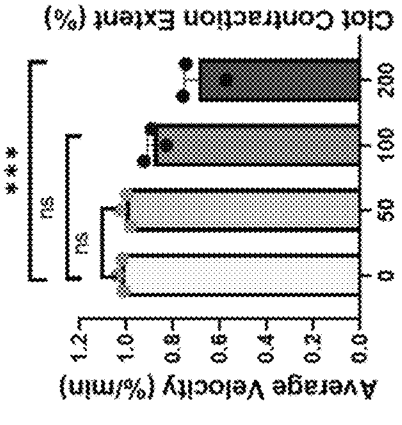
Figure 7D:
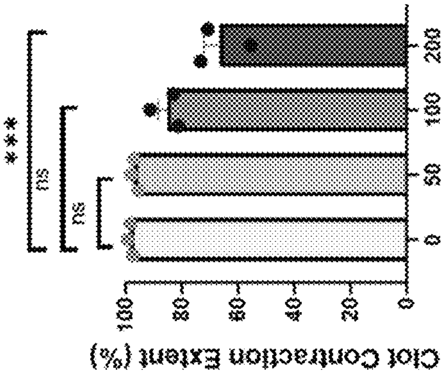
Figure 7E:
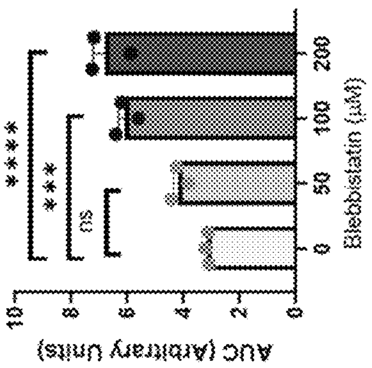
Figure 8A:
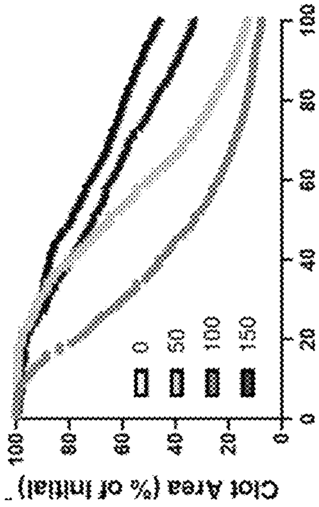
FIGS. 8A-E show the role of $\alpha_{IIb}\beta_3$ integrin in clot contraction.
Figure 8B:
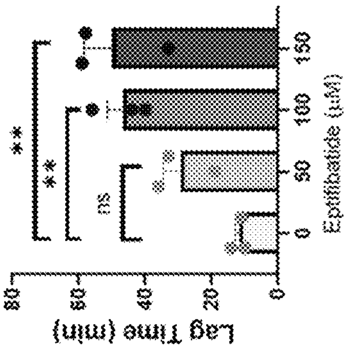
Figure 8C:
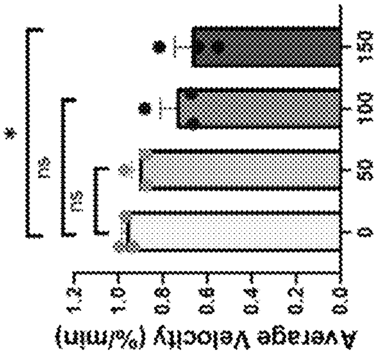
Figure 8D:
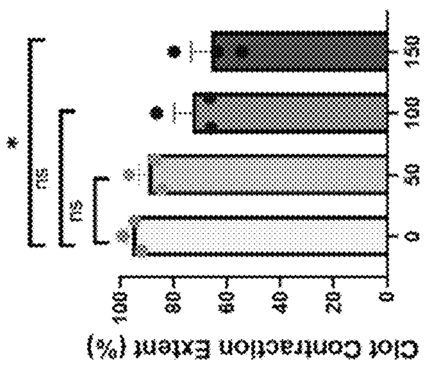
Figure 8E:
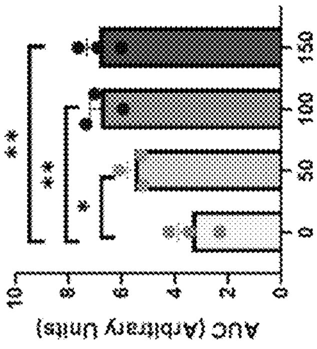
Figure 9A:
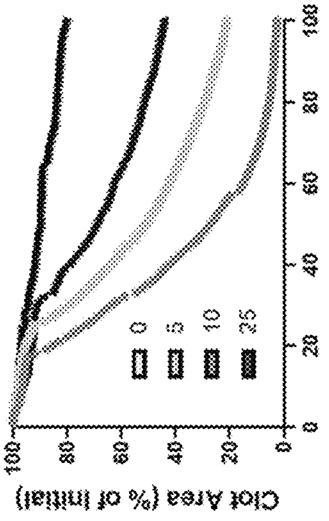
FIGS. 9A-E show the role of glucose metabolism in clot contraction.
Figure 9B:
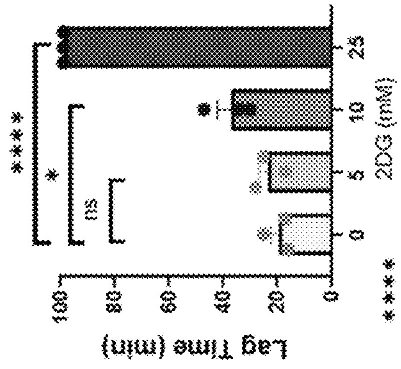
Figure 9C:
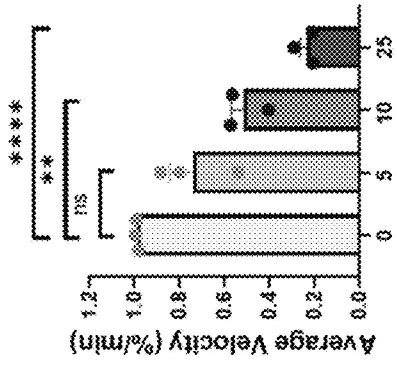
Figure 9D:
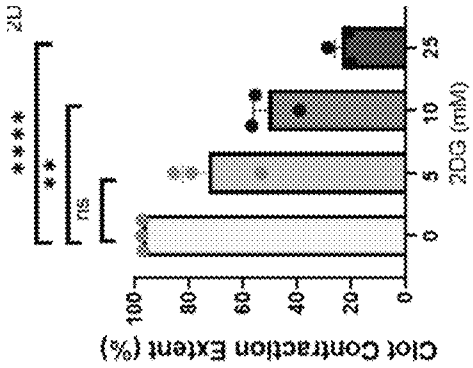
Figure 9E:
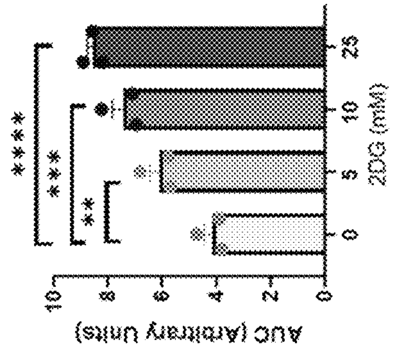

FIGS. 7A-E show the role of Myosin IIA in clot contraction. FIG. 7A shows representative contraction in the presence of the indicated concentrations of blebbistatin, a selective myosin IIA inhibitor, under standard conditions (20 mU/mL thrombin, 250 μg/mL fibrinogen, 0.5 mM $CaCl_2$, and $50\times10^6$/mL washed mouse platelets). The lag time (min; FIG. 7B), average velocity of contraction (%/min; FIG. 7C), extent of contraction (100×(1−% Area at $t_{end}$); FIG. 7D), and AUC (FIG. 7E) were calculated and plotted. Error bars show SEM for n=3; not significant: ns; P≤0.05: *; P≤0.01: ; P≤0.001: *P≤0.0001: **** when compared to no blebbistatin. Statistical significance was calculated using GraphPad Prism.

FIG. 8 shows the role of $\alpha_{IIb}\beta_3$ integrin in clot contraction. FIG. 8A shows representative contraction in the presence of the indicated concentrations of eptifibatide, a competitive inhibitor of fibrin/fibrinogen binding to $\alpha_{IIb}\beta_3$, under standard conditions (20 mU/mL thrombin, 250 μg/mL fibrinogen, 0.5 mM $CaCl_2$, and $50\times10^6$/mL washed mouse platelets). The lag time (min; FIG. 8B), average velocity of contraction (%/min; FIG. 8C), extent of contraction (100×(1−% Area at $t_{end}$); FIG. 8D), and AUC (FIG. 8E) were calculated and plotted. Error bars show SEM for n=3; not significant: ns; P≤0.05: *; P≤0.01: ** when compared to no eptifibatide. Statistical significance was calculated using GraphPad Prism.

FIG. 9 shows the role of glucose metabolism in clot contraction: FIG. 9A shows representative contraction in the presence of the indicated concentrations of 2-deoxyglucose (2DG), an inhibitor of glycolysis (specifically phosphoglucoisomerase), under standard conditions (20 mU/mL thrombin, 250 μg/mL fibrinogen, 0.5 mM $CaCl_2$, and $50\times10^6$/mL washed mouse platelets). The lag time (min; FIG. 9B), average velocity of contraction (%/min; FIG. 9C), extent of contraction (100×(1−% Area at $t_{end}$); FIG. 9D), and AUC (FIG. 9E) were calculated and plotted. Error bars show SEM for n=3; not significant: ns; P≤0.05: *; P≤0.01: ; P≤0.001: * when compared to no 2DG. Statistical significance was calculated using GraphPad Prism.

Also provided are one or more user interfaces for measuring platelet-fibrin clot contraction kinetics. When the "PROCTUBE" option is selected, embodiments provide an option for a user to choose a folder in which the raw photos are saved. Sometimes, if the reaction chamber profiles are small as compared to the whole view field of the images, images can be cropped to get rid of parts of the images that do not contain the reaction chamber profiles and are otherwise noise. In some aspects, the software may include an option to crop images. This crop operation can crop all raw photos in the same dataset (folder) the same way. One can also use other software to crop the raw photos in the same dataset in the same way. When the "PROCTUBE-CROPPED" option is selected, embodiments provide an option for a user to choose a folder in which the cropped photos are saved. When the folder with either raw or cropped pictures is selected, the photos may be processed, clots recognized, clot side-view projection area quantified (in pixels) and written into a table or spreadsheet, and a set of new, analyzed pictures created with the clot profiles identified.

FIG. 10 depicts components of a remote computing device 104, according to embodiments described herein. As illustrated, the remote computing device 104 includes a processor 830, an input/output hardware 832, a network interface hardware 834, a data storage component 836 (which stores image data 838*a* and/or processing data 838*b*), and a memory component 140. The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD) (whether local or cloud-based), and/or other types of non-transitory computer-readable medium. Depending on the particular embodiment, these non-transitory computer-readable mediums may reside within the remote computing device 104 and/or external to the remote computing device 104.

The memory component 140 may store operating logic 842, the image capture logic 144*a*, the image processing logic 144*b*, and the analysis logic 144*c*. Each of these logic components may include a plurality of different pieces of logic, each of which may be embodied as a computer program, firmware, and/or hardware, as an example. A local communication interface 846 is also included in FIG. 10 and may be implemented as a bus or other communication interface to facilitate communication among the components of the remote computing device 104.

The processor 830 may include any processing component operable to receive and execute instructions (such as from a data storage component 836 and/or the memory component 140). As described above, the input/output hardware 832 may include and/or be configured to interface with speakers, microphones, and/or other input/output components.

The network interface hardware 834 may include and/or be configured for communicating with any wired or wireless networking hardware, including an antenna, a modem, a LAN port, wireless fidelity (Wi-Fi) card, WiMAX card, mobile communications hardware, and/or other hardware for communicating with other networks and/or devices. From this connection, communication may be facilitated between the remote computing device 104 and other computing devices.

The operating logic 842 may include an operating system and/or other software for managing components of the remote computing device 104. As discussed above, the image capture logic 144*a* may reside in the memory component 140 and may be configured to cause the processor 830 to receive imagery from the image capture device 102, as well as edit and/or otherwise manage the imagery. The image processing logic (PROCTUBE LOGIC in FIG. 10) 144*b* may be configured to cause the processor 830 to analyze the imagery and perform other functionality described here.

It should be understood that while the components in FIG. 10 are illustrated as residing within the remote computing device 104, this is merely an example. In some embodiments, one or more of the components may reside external to the remote computing device 104 or within other devices. It should also be understood that, while the remote computing device 104 is illustrated as a single device, this is also merely an example. In some embodiments, the image capture logic 144*a*, the image processing logic 144*b*, and the analysis logic 144*c* may reside on different devices.

As an example, one or more of the functionalities and/or components described herein may be provided by the remote computing device 104 and/or the image capture device 102. As such, either of these devices may have similar components as those depicted in FIG. 10. To this end, any of these devices may include logic for performing the functionality described herein.

Additionally, while the remote computing device 104 is illustrated with the image capture logic 144*a*, the image processing logic 144*b*, and the analysis logic 144*c* as separate logical components, this is also an example. In some embodiments, a single piece of logic may provide the described functionality. It should also be understood that while the image capture logic 144*a*, the image processing logic 144*b*, and the analysis logic 144*c* are described herein as the logical components, this is also an example. Other components may also be included, depending on the embodiment.

Methods of Preparation

In some aspects, the present disclosure concerns methods for preparing reaction chambers for observing and/or measuring clot formation and/or contraction. In some aspects, the methods may include cleaning the reaction chamber. It will be appreciated that any contaminant present in the reaction chamber can impact clot formation and/or contraction. Cleaning techniques may depend on the material of the reaction chamber itself. In some aspects, the reaction chamber may be sterilized, such as through heat sterilization, steam sterilization, autoclaving, alcohol wash/soak, or similar known techniques.

In further aspects, the methods of the present disclosure may include preparing an acrylamide pad or plug on the bottom of the reaction chamber. The density of the acrylamide can be adjusted as needed. In some aspects, the acrylamide pad/plug is of about 5% to about 20% acrylamide gel, including 6, 7, 8, 9, 10, 11, 12, 13, 14, 15, 16, 17, 18, and 19%. Such can be prepared by mixing the required amount of acrylamide in an aqueous solution or buffer and adding an initiator such as ammonium persulfate and/or TEMED (tetramethylethylenediamine) to start crosslinking the acrylamide molecules. In order to allow for a smooth top to the acrylamide pad/plug, it may be of benefit to cover the dispensed acrylamide with an immiscible solution, such as distilled water, during crosslinking and then wash or rinse the polymerized acrylamide pad/plug with the reaction medium to be used.

For the preparation of the clotting reagents, components can be added separately to each reaction chamber or can be dispensed from a master suspension. In order for clot to form within the reaction chamber, all of calcium, platelets, fibrinogen and thrombin must be present. In some aspects, thrombin may be replaced and supplemented with an additional protease, such as batroxobin/reptilase, that will cleave fibrinogen to make fibrin but will not activate platelets. Often a master suspension that includes calcium, fibrinogen, and platelets is prepared within a master chamber and gently mixed therein, an aliquot is dispensed to each intermediate chamber, then thrombin added and the whole reaction mixture gently mixed right before transferring the whole reaction mixture to the reaction chamber and starting the time lapse image recording. The preparation of the reaction chamber may accordingly vary depending on what aspects of clot formation and/or contraction are to be observed and/or measured. For example, if a user wants to observe the effects of varying concentrations of thrombin, a master calcium, fibrinogen, and platelet suspension can be made, an aliquot dispended to each intermediate chamber, and then varying amounts of thrombin added right before transferring the whole reaction mixture to the reaction chamber and starting the time lapse image recording. If a user wants to observe the effects of a further test agent or agents on the clot formation and/or contraction, a master calcium, fibrinogen, and platelet suspension can be made, an aliquot dispended to each intermediate chamber, the agent(s) to be further tested added at a desired time, and thrombin added right before transferring the whole reaction mixture to the reaction chamber and starting the time lapse image recording. Accordingly, in some aspects, the reaction chamber may be prepared with one or more of isolated/washed/purified platelets, fibrinogen, calcium or calcium ions such as from calcium chloride salt, and thrombin. In some aspects, the reaction chamber may be prepared with two or more of isolated/washed/purified platelets, fibrinogen, calcium or calcium ions such as from calcium chloride salt, and thrombin. In further aspects, the reaction chamber may be prepared with three or more of isolated/washed/purified platelets, fibrinogen, calcium or calcium ions such as from calcium chloride salt, and thrombin.

In some aspects, the methods may include the presence or addition of a further compound to the reaction chamber, such as a test compound, an agonist for clot formation and/or contraction, and/or an antagonist for clot formation and/or contraction.

As also discussed herein, the reaction chambers may optionally contain additional elements, such as salts and/or buffers. In some aspects, the reaction chambers may be tittered to a particular pH. In other aspects, the reaction chambers may be prepared with other clotting components that may be of interest in the role in affecting clot formation and/or contraction. It will be apparent to those preparing the reaction chambers that the concentration should be maintained across all reaction chambers or a portion thereof if the additional component is being controlled or partially controlled in the clot formation and/or contraction, or can be varied across all reaction chambers or portions thereof if it is being assessed as a variable in clot formation and/or contraction.

Methods of Use

In some aspects, the present disclosure concerns the methods of using the clot observing device as set forth herein to observe and/or measure the formation and/or contraction of clots in the reaction chambers. In some aspects, the reaction chambers are prepared and spaced in a linear (straight or curved) arrangement, such that the image capturing device placed at a fixed distance is able to capture the profile of each reaction chamber. In some aspects, the image capture device is arranged perpendicularly to the plane of the array of the reaction chambers. In some aspects, the image capturing device is positioned at a constant or fixed distance from the reaction chambers. In certain aspects, the image capturing device is arranged to capture profile images of the reaction chambers.

In some aspects of the present disclosure, the reaction chambers are arranged in a linear strip in a dark environment or an environment with limited or controlled light. In certain aspects, the aperture of the light source is the only source of light for illuminating the reaction chambers. In particular aspects, the reaction chambers are in a darkroom or an enclosed chamber that is impermeable or near-impermeable to ambient light. The reaction chambers are illuminated by light passing through the apertures, or by light diffused as it passes from the light source through the aperture made of a translucent or diffusing material and to the reaction chambers.

In some aspects, the clot formation and/or contraction can be initiated once the reaction chambers are positioned or at a time point proximal thereto. Clot formation and/or contraction can be initiated simultaneously or in a staggered fashion, per the user's preference. In some aspects, the user may mark a zero time point or starting point for the reaction chambers or each individual reaction chamber or groupings therein.

In some aspects, the image capturing device may capture an image of each reaction chamber at a time zero or proximal thereto, or at a predetermined or measured time point thereafter. In some aspects, the image capturing device may acquire images of the reaction chamber at multiple time points during the time course of initiation of clot formation through to the completion of clot contraction.

In some aspects, the methods of using the clot observing device may include initiating the process of clot contraction. As identified herein, the presence of platelets, fibrinogen, calcium and thrombin are required for clot formation and/or contraction to occur. In certain aspects, initiation may be considered at a time point when all four components are together in the same solution, such as within the same reaction chamber. In some aspects, one or more of thrombin, fibrinogen, calcium and/or platelets are added to the reaction chamber to initiate clot formation and/or contraction (see, e.g., Prakhya et al. *Platelets.* 2023 Dec; 34(1):2222184. PMID: 37292023; and, Prakhya. *Res Pract Thromb Haemost.* 2022. 6(5):e12755, both incorporated by reference herein).

In some aspects of the present disclosure, the methods include processing images obtained by the image capturing device to determine data or information concerning the clot, such as the clot side-view projection area, rate of formation, rate of contraction, as well as comparative data as to effects caused by difference between different treatments, different concentrations, different volumes, different temperatures and similar.

In some aspects, the images obtained by the image capture device are processed through digital analytical tools to create further data, including recognition of edges of the clot side-view profile, measurements of clot side-view projection area, as well as assembled into a viewable film or sequence of images over the time course. As described herein, developed software for the device can assign points within a captured image that delineate the edges or outer boundaries of the clot silhouette and calculate the area enclosed therein to assign a clot side-view projection area value for each image.

In some aspects, the arrangement may include an interface that calculates the information of clot size and/or rate of clot contraction for the user. In some aspects, the device may include an interface that identifies the time zero or initiation point for allowing clot contraction in one or more reaction chambers. In some aspects, the arrangement may include an interface to adjust for image quality or to smooth data presented. In some aspects, the arrangement may include an interface that assembles collected images into a film or video. In some aspects, an interface may be included that collects and processes data from multiple reactions, such as in repeated experiments. In such instances, the interface may provide mean, standard error of mean, standard deviation, and similar statistical calculations.

In some aspects, the presence of multiple reaction chambers allows for comparison between reactions. For example, as set forth herein, test compounds can be evaluated on their affect in clot contraction. Comparison between concentrations and/or controls allows for confidence in an observed result. Furthermore, comparison allows for identification of potential differences between different sources of clotting materials. For example, platelets and/or PRP can be collected from multiple subjects, such as human subjects. Differences in clotting in patient subpopulations can identify potential conditions or clotting differences that can then allow for a new or adjusted line of therapy for most suitable patient groups.

EXAMPLES

Preparation of Reaction Chambers: Critical to the measurements are the reaction chambers (FIG. 3B). They must be thoroughly cleaned, inside and out, and have an acrylamide plug on the inner bottom so that the clot contracts upward toward the solution meniscus. Siliconized glass tubes (Chrono-Log P/N 312 cuvettes; Havertown, PA) were soaked in distilled water followed by 95% ethanol for 5 min each, and then air-dried. The acrylamide solution for making pads for 12 tubes was: 2 mL of 10% polyacrylamide prepared by mixing 667 μL of acrylamide (IBI InstaPAGE Acrylamide 40% Solution, 37.5:1; New Haven, CT), 500 μL Protogel resolving buffer (National Diagnostics, EC-892 resolving gel) and 832 μL distilled water. Polymerization was initiated with 9 μL 10% ammonium persulfate and 2 μL TEMED. Immediately afterwards, 100 μL of the mixture was transferred, using a gel-loading tip, to the bottom of each glass tube without touching the tube wall. The gel mixture was topped with 10 μL of distilled water and allowed to polymerize for ~2 h. The tubes were gently rinsed, twice, with 300 μL HEPES-Tyrode buffer (pH 7.4), to remove un-reacted polyacrylamide and solutes.

Platelet Preparations: PRP or washed platelets were prepared from mice or human whole blood as described (Ren et al. 2007; Banerjee et al. 2019). For mouse platelets, an anticoagulant master mix (100 μL) is drawn into a 1 mL tuberculin slip tip syringe with a 26G ⅜ needle, so that the final concentrations in 1 mL of blood was 0.38% sodium citrate, 0.2 U/mL apyrase, and 10 ng/mL $PGI_2$. The animals were euthanatized via $CO_2$ asphyxiation and blood was immediately harvested by cardiac puncture. After drawing, the needle was removed, and the harvested blood was expelled into an Eppendorf tube and mixed gently by inversion. Blood was pooled, diluted 1:1 (v/v) with PBS or HEPES-Tyrode buffer (pH 6.5) containing 0.2 U/mL apyrase and 10 ng/mL $PGI_2$, and incubated for 5 min. PRP was harvested from blood by centrifugation at 215×g in a swinging-bucket rotor centrifuge (Beckman Coulter Avanti J-15R centrifuge with acceleration and deceleration set as 5 and 2, respectively) for 5 min. PRP was removed, transferred to new tube. Platelets were harvested from PRP by centrifugation at 675×g for 7-10 min. The pelleted platelets were washed by gently re-suspension in 1-2 mL HEPES-Tyrode buffer (pH 6.5) supplemented with 1 mM EGTA, 0.2 U/mL apyrase and 10 ng/mL $PGI_2$, using large disposable transfer pipets, and centrifugation at 675×g for 7 min. The washed platelets were finally resuspended in 1-2 mL HEPES-Tyrode buffer (pH 7.4), and their concentrations were measured using a Z2 Coulter Particle Count and Size Analyzer (Beckman Coulter, Indianapolis, IN). The platelet concentrations were adjusted as needed with HEPES-Tyrode buffer (pH 7.4) and incubated at room temperature (RT) or 37° C. for 30 min to dissipate the residual effects of $PGI_2$ before setting up the clot contraction assay.

Optimization of Clot Contraction Assay Conditions: Using washed platelets offers the most experimental flexibility, but assay conditions should be standardized to obtained consistent results. Platelet number, fibrinogen, and calcium concentrations should all be optimized. For these studies, fibrinogen (Sigma F4883, 10 mg/mL stock, made fresh) and $CaCl_2$ (from a 500 mM stock), were added to an Eppendorf tube before starting the assay with thrombin (from a 10 U/mL stock; Chrono-par thrombin #386, Chrono-Log, Haverton PA) and immediately transferring the reactions to prepared reaction chambers. The camera was adjusted, and image acquisition was started. Blebbistatin, eptifibatide, and 2DG were added independently to platelet-containing reactions prior to addition of fibrinogen, $CaCl_2$, and thrombin to probe the importance of myosin IIA, fibrin-integrin interaction, and glucose metabolism, respectively.

Image Processing and Clot Analysis: The images captured during each experiment were copied into a single folder. Raw, cropped or processed image stacks can be made into movies using several imaging tools. ImageJ was used to create macros, which cropped images, and to make movies from either the whole set or a subset of an experiment's images. For quantitative analysis of the raw or cropped images, we created a custom software (available at dropbox.com/sh/nce88konldxwzfa/AACn-ZbPO1Dep-wk0k76cErFa?dl=0) to recognize and quantify the clot side-view projection area for each image. Earlier attempts using threshold-based image segregation to recognize clots in the time-lapse images generated variable results, thus a machine learning/neural network-based image segregation approach was taken. The resulting software, "PROCTUBE", can be opened by double-clicking the executable file or by typing in the command window "proctube" or "proctube-m [modelfile]". For cropped image datasets, "PROCTUBE-CROPPED" is used. If needed, "-ct"/"-cb"/"-cl"/"-cr" command line options can be specified to crop out undesired top/bottom/left/right portions from the image datasets so that the software can focus more on the tubes. E.g. "proctube-ct 300-cb 200". When the software starts, a box or window opens in which you are directed to select the folder with the saved raw or cropped images from your experiment. The software runs from the last image in the sequence and tracks backwards. The "PROCTUBE" or "PROCTUBE-CROPPED" software outputs images with the edges of recognized clots drawn (blue outline) and areas of the clots quantified (in pixels), as well as a spreadsheet file containing all quantified clot areas for each image. These images and the table are saved in the same folder as the input images. The data in the spreadsheet were converted to clot area (% of initial) and plotted against time in GraphPad Prism (8.4.3; FIGS. 2C and 2D).

Kinetics and Statistical Analyses: The percent clot areas at given time points ($Y_t$) are then obtained by dividing measured clot area values by the area of unstimulated platelets measured at time zero, then multiplied by 100. FIGS. 2C-2E demonstrate changes in clot contraction in the obtained images at two different time points (0 min and 70 min). Image data were analyzed computationally (using GraphPad and Excel) to determine the lag time (initial time at which the point-to-point change in clot area exceeds 1%); area under the curve (calculated with GraphPad); clot contraction extent (relative clot size at a defined endpoint, e.g., 100 min) and average velocity (average of the first derivative of the smoothed curve over the entire time course; see FIG. 3A, calculated with GraphPad Prism 8.4.3). To better understand different stages of clot contraction, a piece-wise analysis was carried out by dividing the curve into 3 phases based on a plot of the curve's first derivative (FIG. 3A). As was previously shown by Tutwiler et al. (Blood 127(1): 149-159, 2016, doi.org/10.1182/blood-2015-05-647560), using this piece-wise analysis allows for the calculation of rates and clot contraction % for each phase of the curve. The transition times for phases 1-to-2 and 2-to-3, $t_1$ and $t_2$, were determined from the local maxima and minima of the first derivatives of the smoothened clot contraction curve. The size of the smoothening window was determined based on the time resolution of the raw data and the kinetics of the process. We chose to smoothen with 10 neighbors on each side. The initial or initiation phase ($t_0$-$t_1$) was fit to an exponential equation; the second or contraction phase ($t_1$-$t_2$) was fit to a linear equation; and the third or stabilization phase ($t_2$-$t_{end}$) was fit to an exponential equation, and the rates ($k_1$, $k_2$, and $k_3$) for each phase of the contraction curve were calculated using available software and the following equations.

Initiation Phase $t_0<t<t_1\ y=y_0-(y_0-y_1)(1-e^{-k_1t})$ Phase 1:

Contraction Phase $t_1<t<t_2\ y=y_1-k_2t$ Phase 2:

Stabilization Phase $t_2<t<t_{end}\ y=y_2-(y_2-y_3)(1-e^{-k_3t})$ Phase 3:

Statistical significance was assessed using one-way ANOVA followed by a multiple comparison test with the Bonferroni method.

Figure 3F:
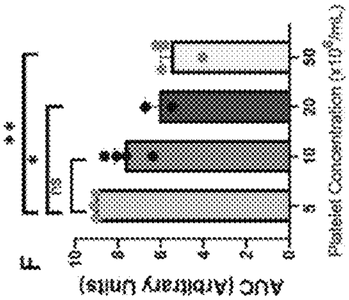

Optimizing Assay Conditions: Clot contraction is affected by the concentrations of platelets, calcium, thrombin, and fibrinogen. Initially, different concentrations of washed mouse platelets were tested, stimulated with thrombin (20 mU/mL) and fibrinogen (250 μg/mL). Platelet concentrations between 5 and $50\times10^6$/mL had a significant decrease in lag time as counts increased (FIGS. 3B and 3C). The average velocity and clot contraction extent increased and was the highest at $50\times10^6$ platelets/mL (FIGS. 3D, 3E, and 3F). Similar results were seen when each of the three phases: initiation (Phase 1), contraction (Phase 2), and stabilization (Phase 3), were analyzed, though at the lowest platelet concentration used, none of the phases were readily detected from the data. Given the robust contraction rate and clear delineation of all three phases, $50\times10^6$ platelets/mL was chosen for the standard assay conditions.

To address the calcium dependence, the concentration of exogenously supplied $CaCl_2$ was varied from 0-1 mM and clotting was initiated with 20 mU/mL thrombin in the presence of 250 μg/mL fibrinogen (FIGS. 4A-4E). EGTA was added to the platelet preparation washes but not to the final suspensions unless indicated. While there were limited differences in clot contraction when calcium was included (between 0.1 and 1 mM), the average contraction velocity was only significantly reduced when EGTA was included. Phase 1 was most affected by increasing calcium concentrations and none of the three phases was detectible in the presence of EGTA. These results mirror previous reports using the HemaCore Thrombodynamics Analyzer. Since calcium was required for optimal contraction using our platelet preparation protocol, 0.5 mM was chosen as the standard concentration for later experiments.

Next tested was the importance of thrombin, which was varied from 10-200 mU/mL (FIGS. 2C-2E and 5A-5E). As expected, with increased thrombin concentration, the extent of clot contraction remained unchanged but the lag time, which is indicative of clot initiation decreased. Phase 1, initiation, was most affected by increased thrombin, with its rate increasing ~5-fold over the concentration range tested (see Table 1). Based on these data, 20 mU/mL thrombin was chosen as the standard concentration for subsequent assays.

Cross-linking of fibrin and attachment of platelets to fibers are important steps in clot contraction. Thus, the ratio of platelets to fibrinogen is critical in determining the rate and extent of contraction. When clot contraction was initiated without added fibrinogen, the average velocity and extent were severely affected, suggesting the platelet pools of fibrinogen are insufficient (FIGS. 6A-6E). Fibrinogen levels were tested varying from 62.5 to 1,000 μg/mL, which, although lower than physiological levels, provided a sensitive window for the assay. The extent of clot contraction and average velocity of contraction were highest at 125 and 250 μg/mL. At the highest fibrinogen concentration (1,000 μg/mL), the fibrinogen/platelet ratio was too high for efficient contraction. When fibrinogen was omitted, none of the three phases were detectible. Thus, for standard conditions, we chose 250 μg/mL, which showed the best average velocity and extent of contraction.

Based on these titrations, $50\times10^6$ platelets/mL, 0.5 mM $CaCl_2$, 20 mU/mL thrombin, and 250 μg/mL fibrinogen, at room temperature, were used as the standard reaction conditions for washed mouse platelets. This yielded a predictable lag time, average velocity, extent, and AUC, all of which could be compared across treatment groups. Additionally, all three phases of the contraction process (initiation, contraction, and stabilization) were readily detectible. Optimizing these parameters: platelet number, calcium, fibrinogen, and agonist (i.e., thrombin), when using this system is recommended to tailor it to the experimental questions being asked and to assure that all three phases are detected and can be compared.

Troubleshooting: There are some predictable problems with the assay setup that can be mitigated. For example, if a clot falls off the meniscus, it should not be included in the analysis, regardless of whether the software is able to detect it or not. Though this occurred randomly, thoroughly cleaning of the tubes lessens the chance. The camera position needs to be consistent and the shooting angle needs to be horizontal so that the clot images are correctly and more easily recognized and processed. This requires some optimization using both the camera and the image processing software. It is suggested to have a dedicated place for experiments. Stray light (e.g., reflections) can be a problem because it causes streaks on the tube surfaces, which may be misread by the software. It is best to place the equipment in a dark room or in a box that can be isolated from external light sources.

Myosin IIA and Integrins are Important for Clot Contraction: Previous reports have demonstrated the importance of myosin IIA and fibrin-integrin interaction to clot contraction. The methods were applied to determine if this system recapitulated these dependencies. Use of blebbistatin, a selective myosin IIA inhibitor and its addition (50 to 200 μM) resulted in a dose-dependent increase in lag time and decrease in average velocity and extent of clot contraction (FIGS. 7A-7E). There was also a drastic decrease in the Phase 2 contraction rate. These results confirm the importance of platelet myosin IIA-based force generation to clot contraction and indicate that the rate of clot contraction (Phase 2) is sensitive to defective platelet myosin IIA.

Integrin $\alpha_{IIb}\beta_3$ is expressed at high levels in platelets and the fibrin-integrin $\alpha_{IIb}\beta_3$ interaction is crucial for development of clot tension. To demonstrate the role of fibrin-integrin $\alpha_{IIb}\beta_3$ interaction in clot contraction, the effect of eptifibatide, a cyclic heptapeptide derived from southeastern pygmy rattlesnake venom and a natural competitive inhibitor of fibrin/fibrinogen binding to $\alpha_{IIb}\beta_3$ was tested. Addition of 50 to 150 μM resulted in a dose-dependent decrease in extent and average velocity of contraction (FIGS. 8A-8E). At this dosage range, there was a ~4-fold increase in lag time (Table 2). At the highest dosage (150 μM), none of the three phases were detectible. These results confirm the importance of fibrin-$\alpha_{IIb}\beta_3$ interaction to clot contraction and show that our assay system recapitulated previously reported results.

Glucose Metabolism is Important for Clot Contraction: Clot contraction is an actomyosin-dependent process that utilizes energy released by the ATP hydrolysis. Earlier reports, using conventional, qualitative approaches, showed that both glycolysis and oxidative phosphorylation (OxPhos) contribute to the energy needs for platelet function. To better understand the role of platelet bioenergetics in clot contraction, we applied our method to investigate how glycolysis affects clot contraction. 2DG, a glucose analog and inhibitor of phosphoglucoisomerase, was titrated in this assay. Time courses of clot contraction at varying 2DG concentrations showed prolonged lag time and significant inhibitory effects on average velocity and extent of contraction (FIGS. 9A-9E). At the highest concentration (25 mM), none of the three phases were detectible. Interesting, Phase 3 seemed most affected, even at the lower concentrations (rate reduced by ~5-fold with 10 mM 2DG; Table 2). These results show that clot contraction relies on glycolysis and our method can be used to study the effects of metabolic inhibitors on platelet bioenergetics.

Clot contraction is important for hemostasis since it promotes wound closure; and it also maintains vessel patency by reducing the size of potentially occlusive thrombi. However, the mechanistic understanding of clot contraction is limited, in part, due to limitations in the tools available to quantitatively define the process. Here we report a sensitive and flexible method to assay clot contraction kinetics for multiple samples using a low-cost set-up (<$1,000) and a robust clot recognition and quantification software. This assay system showed the expected dependence of clot contraction on platelet number, fibrinogen, calcium, thrombin, myosin IIA and fibrin-integrin $\alpha_{IIb}\beta_3$ interaction. Herein is demonstrated how this assay system could be utilized to investigate the dependency of clot contraction on platelet bioenergetics, e.g., glycolysis. This system is a cost-effective digital version of an old concept (Henry Ford Hospital Medical Bulletin, 1960; Osdoit & Rosa, 2001). The methods set forth herein can facilitate the molecular dissection of the mechanisms and modulators of clot contraction, thus defining how dysfunction in clot contraction affects bleeding diatheses or occlusive thrombosis.

Although simple, the methods do require careful implementation with the following being most important: 1) use and cleanliness of the Chrono-Log aggregometer tubes, which have already been widely used for platelet aggregation studies, 2) use of an acrylamide pad on the bottom of the Chrono-Log aggregometer tubes, 3) bottom illumination, 4) selection of a digital camera with an intervalometer and close-up features, 5) camera positions and setup, and 6) elimination of stray light. All are important for generating quality images for analysis. Gentle and thorough mixing after adding thrombin is necessary for uniform clot formation and/or contraction. As samples are loaded sequentially, one should consider the time delay caused by sample loading into each tube when comparing lag times. This system is readily adaptable to both human and rodent washed platelets and PRP; however, conditions should be re-optimized when switching to different preparations of platelets including whole blood. Finally, in these studies, room temperature (~25° C.) was used; however, the assays can be performed at 37° C., as needed.

This system allows for the testing of multiple treatment conditions using the same preparation of platelets. Such adaptability is valuable when determining the relative effects of platelet pathways (i.e., signaling, secretion, or bioenergetics) or of different therapeutics. Samples can be run in duplicate or triplicate given the possibility for multiple tubes, enhancing the statistical power. This system is also useful when phenotyping transgenic mouse platelets when ideally blood from each mouse, amount of which is limited, is tested individually to assess individual variability. Thus, this system is ideal for addressing basic mechanistic questions. These assay measures the bulk properties of a population of platelets, but the data generated can augment the recent innovative biophysical methods performed on single platelets using advanced imaging techniques, since our system is a more facile and less instrument-intensive way to scan treatments to identify optimal conditions for downstream detailed analysis. In short, this assay system is seen as a "workhorse" tool with which to better understand the molecular features of how platelets mediate clot contraction. Further development for clinical usages and/or medium throughput laboratory testing and drug screens is underway.

Tutwiler et al. stated that "*Blood clot contraction remains the least studied stage of blood clotting* (Arteriosclerosis, thrombosis, and vascular biology 37(2): 271-279, 2017 doi.org/10.1161/ATVBAHA.116.308622). This is perhaps, in part, due to limitation in the generally used methods to evaluate the process. While some requirements for clot contraction have a clear logic (e.g., thrombin, fibrinogen, calcium) and genetic diseases associated with cytoskeleton (e.g., Wiskot-Aldrich and May-Heglin Syndromes) or integrins (e.g., Glanzmann's thrombasthenia) have clear mechanistic explanations, there are examples of contraction dysfunction yet to be understood. For example, in stroke patients, there is a post-stroke clot contraction defect (Tutwiler, Peshkova, et al., 2017). One plausible explanation given was metabolic exhaustion of the platelets, which is consistent with our studies showing that glucose metabolism is important for normal clot contraction. It is hoped that this sensitive and flexible system, with its multi-sample capacity, robust software and low-cost, will give investigators a valuable tool to further define this aspect of platelet function and determine what leads to contraction dysfunction in human diseases/conditions.

The foregoing description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of ordinary skill in the art.

The terminology used herein is for the purpose of describing particular embodiments only and is not intended to be limiting. As used herein, the singular forms "a", "an", and "the" are intended to include the plural forms, including "at least one," unless the content clearly indicates otherwise. "Or" means "and/or". As used herein, the term "and/or" includes any and all combinations of one or more of the associated listed items. It will be further understood that the terms "comprises" and/or "comprising", or "includes" and/or "including" when used in this specification, specify the presence of stated features, regions, integers, steps, operations, elements, components, and/or groups, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Patents, applications, and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular aspects of the invention, but is not meant to be a limitation upon the practice thereof. The following claims, including all equivalents thereof, are intended to define the scope of the invention.

TABLE 1

| Cell number ($\times 10^6$) | Lag time (min) | Average Velocity (%/min) | Clot Contraction Extent (%) | AUC (AU) | PHASE 1 % Contraction | PHASE 1 Rate 1 ($\times 10^{-3}$ %/min) | PHASE 1 $t_1$ (min) | PHASE 2 % Contraction | PHASE 2 Rate 2 (%/min) | PHASE 2 $t_2$ (min) | PHASE 3 % Contraction | PHASE 3 Rate 3 ($\times 10^{-2}$ %/min) |
|---|---|---|---|---|---|---|---|---|---|---|---|---|
| 5 | 97.33 ± 1.44 | 0.32 ± 0.05 | 31.38 ± 5.08 | 9.06 ± 0.02 | N/D | N/D | N/D | N/D | N/D | N/D | N/D | N/D |
| 10 | 63.25 ± 13.74 | 0.62 ± 0.08 | 60.65 ± 8.10 | 7.68 ± 0.48 | 2.49 ± 0.75 | 1.28 ± 0.61 | 19.50 ± 4.21 | 25.30 ± 4.59 | 0.57 ± 0.14 | 66 ± 8.16 | 32.87 ± 8.63 | 1.83 ± 0.49 |
| 20 | 31.00 ± 0.71 | 0.82 ± 0.09 | 80 ± 8.33 | 6.11 ± 0.43 | 1.66 ± 0.81 | 0.65 ± 0.25 | 17.50 ± 1.77 | 19.86 ± 1.31 | 0.92 ± 0.10 | 39 ± 0.71 | 58.48 ± 6.21 | 2.7 ± 0.13 |
| 50 | 26.50 ± 2.76 | 0.89 ± 0.04 | 87.27 ± 3.73 | 5.52 ± 0.50 | 1.95 ± 1.17 | 1.76 ± 1.18 | 12 ± 1.22 | 28.19.67 ± 8.31 | 1.03 ± 0.32 | 39.75 ± 2.78 | 57.13 ± 4.31 | 3.83 ± 0.11 |

| $CaCl_2$ (mM) | Lag time (min) | Average Velocity (%/min) | Clot Contraction Extent (%) | AUC (AU) | % Contraction | Rate 1 ($\times 10^{-3}$ %/min) | $t_1$ (min) | % Contraction | Rate 2 (%/min) | $t_2$ (min) | % Contraction | Rate 3 ($\times 10^{-2}$ %/min) |
|---|---|---|---|---|---|---|---|---|---|---|---|---|
| 0 | 16.67 ± 1.86 | 0.95 ± 0.01 | 94.13 ± 1.19 | 4.69 ± 0.09 | 1.44 ± 0.50 | 1.77 ± 0.79 | 9.33 ± 1.20 | 24.73 ± 5.51 | 1.25 ± 0.09 | 28.67 ± 4.48 | 67.97 ± 4.33 | 1.25 ± 0.09 |
| 0.1 | 15.00 ± 1.00 | 0.98 ± 0.01 | 97.02 ± 1.00 | 3.78 ± 0.47 | 2.91 ± 1.30 | 5.00 ± 2.08 | 7.00 ± 1.15 | 29.63 ± 4.51 | 1.51 ± 0.16 | 27.33 ± 2.91 | 64.48 ± 3.05 | 1.51 ± 0.16 |
| 0.5 | 15.67 ± 2.19 | 0.96 ± 0.03 | 95.36 ± 2.20 | 3.93 ± 0.65 | 3.27 ± 1.38 | 4.67 ± 2.33 | 8.33 ± 2.40 | 27.00 ± 3.01 | 1.43 ± 0.11 | 28.00 ± 6.00 | 65.48 ± 5.67 | 1.43 ± 0.11 |
| 1 | 17.67 ± 1.33 | 0.99 ± 0.01 | 98.08 ± 0.38 | 3.69 ± 0.31 | 5.50 ± 2.44 | 5.00 ± 1.73 | 12.33 ± 1.45 | 31.17 ± 0.21 | 1.87 ± 0.22 | 30.00 ± 2.89 | 61.41 ± 2.57 | 1.87 ± 0.22 |
| EGTA | 71.67 ± 10.59 | 0.51 ± 0.05 | 50.72 ± 5.13 | 7.83 ± 0.16 | N/D | N/D | N/D | N/D | N/D | N/D | N/D | N/D |

| Thrombin (mU/mL) | Lag time (min) | Average Velocity (%/min) | Clot Contraction Extent (%) | AUC (AU) | % Contraction | Rate 1 ($\times 10^{-3}$ %/min) | $t_1$ (min) | % Contraction | Rate 2 (%/min) | $t_2$ (min) | % Contraction | Rate 3 ($\times 10^{-2}$ %/min) |
|---|---|---|---|---|---|---|---|---|---|---|---|---|
| 0 | 99.00 ± 0.00 | 0.18 ± 0.03 | 18.63 ± 4.84 | 8.70 ± 0.50 | N/D | N/D | N/D | N/D | N/D | N/D | N/D | N/D |
| 10 | 28.33 ± 1.20 | 0.82 ± 0.15 | 80.19 ± 14.60 | 5.62 ± 1.09 | 4.93 ± 3.10 | 4.27 ± 3.37 | 13.33 ± 3.33 | 23.95 ± 7.88 | 1.02 ± 0.34 | 36.00 ± 1.00 | 51.32 ± 7.45 | 3.93 ± 2.07 |
| 20 | 19.33 ± 2.73 | 0.90 ± 0.05 | 88.45 ± 5.32 | 4.90 ± 0.91 | 4.66 ± 3.57 | 4.67 ± 4.17 | 11.33 ± 0.67 | 31.74 ± 3.50 | 1.33 ± 0.23 | 36.33 ± 4.10 | 52.05 ± 3.37 | 3.63 ± 1.23 |
| 30 | 15.33 ± 1.76 | 0.94 ± 0.02 | 92.41 ± 2.27 | 4.10 ± 0.85 | 6.03 ± 3.23 | 6.67 ± 4.26 | 8.67 ± 0.67 | 20.91 ± 7.58 | 1.67 ± 0.65 | 22.00 ± 2.00 | 65.45 ± 8.50 | 2.70 ± 0.17 |
| 50 | 10.67 ± 4.33 | 0.94 ± 0.02 | 92.51 ± 3.20 | 3.69 ± 1.16 | 6.96 ± 3.70 | 27.33 ± 24.34 | 6.67 ± 2.40 | 16.04 ± 1.79 | 1.97 ± 0.83 | 18.00 ± 5.51 | 69.51 ± 2.77 | 3.10 ± 0.45 |
| 100 | 9.00 ± 3.79 | 0.97 ± 0.00 | 94.93 ± 1.57 | 3.32 ± 0.71 | 6.55 ± 3.07 | 21.33 ± 16.90 | 5.00 ± 2.52 | 19.72 ± 7.67 | 2.02 ± 0.73 | 18.67 ± 8.57 | 68.67 ± 9.45 | 3.43 ± 0.34 |

| Fibrinogen (μg/mL) | Lag time (min) | Average Velocity (%/min) | Clot Contraction Extent (%) | AUC (AU) | % Contraction | Rate 1 ($\times 10^{-3}$ %/min) | $t_1$ (min) | % Contraction | Rate 2 (%/min) | $t_2$ (min) | % Contraction | Rate 3 ($\times 10^{-2}$ %/min) |
|---|---|---|---|---|---|---|---|---|---|---|---|---|
| 0 | 99.00 ± 0.00 | 0.19 ± 0.02 | 18.45 ± 1.62 | 9.05 ± 0.10 | N/D | N/D | N/D | N/D | N/D | N/D | N/D | N/D |
| 62 | 46.67 ± 18.51 | 0.53 ± 0.17 | 53.50 ± 16.43 | 6.66 ± 1.19 | 2.11 ± 0.02 | 1.50 ± 0.29 | 13.00 ± 1.73 | 24.32 ± 9.38 | 1.19 ± 0.28 | 28.00 ± 1.73 | 43.44 ± 7.14 | 2.90 ± 1.33 |
| 125 | 26.40 ± 5.24 | 1.00 ± 0.01 | 98.07 ± 0.40 | 4.13 ± 0.50 | 2.72 ± 0.59 | 2.25 ± 0.51 | 10.75 ± 0.61 | 37.99 ± 3.73 | 1.66 ± 0.12 | 30.75 ± 1.22 | 57.36 ± 3.57 | 5.90 ± 0.27 |
| 250 | 21.67 ± 2.75 | 0.98 ± 0.00 | 96.87 ± 0.66 | 4.23 ± 0.31 | 3.26 ± 0.92 | 2.18 ± 0.74 | 10.40 ± 0.37 | 26.29 ± 4.45 | 1.50 ± 0.16 | 29.40 ± 1.06 | 67.28 ± 4.00 | 4.96 ± 0.32 |
| 500 | 17.80 ± 1.17 | 0.89 ± 0.05 | 88.42 ± 5.64 | 4.89 ± 0.43 | 3.48 ± 0.87 | 2.78 ± 0.84 | 9.40 ± 1.06 | 19.02 ± 3.38 | 1.10 ± 0.14 | 26.00 ± 2.31 | 65.92 ± 4.99 | 3.32 ± 0.58 |
| 1000 | 39.80 ± 13.76 | 0.69 ± 0.11 | 68.91 ± 11.10 | 6.18 ± 0.56 | 4.20 ± 1.18 | 3.03 ± 0.80 | 11.80 ± 0.73 | 10.11 ± 2.55 | 0.70 ± 0.16 | 25.40 ± 1.21 | 54.53 ± 9.30 | 1.92 ± 0.57 |

TABLE 2

| Blebbistatin (μM) | Lag time (min) | Average Velocity (%/min) | Clot Contraction Extent (%) | AUC (AU) | PHASE 1 % Contraction | PHASE 1 Rate 1 ($\times 10^{-3}$ %/min) | PHASE 1 $t_1$ (min) | PHASE 2 % Contraction | PHASE 2 Rate 2 (%/min) | PHASE 2 $t_2$ (min) | PHASE 3 % Contraction | PHASE 3 Rate 3 ($\times 10^{-2}$ %/min) |
|---|---|---|---|---|---|---|---|---|---|---|---|---|
| 0 | 20.67 ± 2.73 | 1.02 ± 0.01 | 98.36 ± 0.50 | 3.15 ± 0.04 | 7.16 ± 1.36 | 5.33 ± 1.86 | 14.33 ± 2.33 | 40.31 ± 7.43 | 2.14 ± 0.43 | 28.67 ± 1.86 | 50.89 ± 6.36 | 5.03 ± 0.39 |
| 50 | 23.33 ± 2.33 | 1.00 ± 0.01 | 96.93 ± 0.75 | 4.18 ± 0.18 | 4.23 ± 0.95 | 3.67 ± 0.88 | 14.33 ± 1.20 | 26.51 ± 2.26 | 1.40 ± 0.13 | 32.00 ± 2.65 | 66.19 ± 1.45 | 5.00 ± 0.53 |
| 100 | 40.00 ± 3.21 | 0.88 ± 0.03 | 85.15 ± 3.11 | 6.08 ± 0.24 | 7.21 ± 2.75 | 4.00 ± 1.15 | 24.67 ± 2.40 | 28.71 ± 6.39 | 1.00 ± 0.07 | 51.00 ± 4.58 | 49.27 ± 2.48 | 3.47 ± 0.82 |
| 200 | 43.67 ± 4.91 | 0.69 ± 0.06 | 66.52 ± 5.54 | 6.79 ± 0.44 | 12.21 ± 3.91 | 5.00 ± 1.00 | 31.00 ± 2.08 | 14.17 ± 3.78 | 0.69 ± 0.15 | 49.33 ± 0.67 | 40.15 ± 7.72 | 1.70 ± 0.38 |

| Eptifibatide (μM) | Lag time (min) | Average Velocity (%/min) | Clot Contraction Extent (%) | AUC (AU) | % Contraction | Rate 1 ($\times 10^{-3}$ %/min) | $t_1$ (min) | % Contraction | Rate 2 (%/min) | $t_2$ (min) | % Contraction | Rate 3 ($\times 10^{-2}$ %/min) |
|---|---|---|---|---|---|---|---|---|---|---|---|---|
| 0 | 11.7 ± 1.20 | 0.97 ± 0.01 | 95.45 ± 2.02 | 3.33 ± 0.55 | 1.56 ± 0.73 | 3.27 ± 1.27 | 6.00 ± 1.00 | 31.36 ± 6.24 | 2.59 ± 0.37 | 20.67 ± 0.67 | 62.53 ± 4.95 | 3.63 ± 0.55 |
| 50 | 29.33 ± 5.24 | 0.91 ± 0.03 | 89.56 ± 3.70 | 5.51 ± 0.29 | 5.36 ± 4.35 | 3.93 ± 1.59 | 14.33 ± 6.98 | 32.14 ± 3.48 | 1.96 ± 0.62 | 43.00 ± 7.00 | 52.91 ± 4.60 | 3.83 ± 1.17 |
| 100 | 46.67 ± 4.81 | 0.74 ± 0.07 | 73.02 ± 6.74 | 6.76 ± 0.41 | 9.24 ± 4.64 | 4.00 ± 1.00 | 26.00 ± 11.37 | 20.75 ± 4.31 | 1.08 ± 0.21 | 52.00 ± 7.57 | 43.03 ± 5.21 | 2.20 ± 0.47 |
| 150 | 50 ± 8.50 | 0.67 ± 0.08 | 66.08 ± 7.37 | 6.84 ± 0.47 | N/D | N/D | N/D | N/D | N/D | N/D | N/D | N/D |

| 2DG (mM) | Lag time (min) | Average Velocity (%/min) | Clot Contraction Extent (%) | AUC (AU) | % Contraction | Rate 1 ($\times 10^{-3}$ %/min) | $t_1$ (min) | % Contraction | Rate 2 (%/min) | $t_2$ (min) | % Contraction | Rate 3 ($\times 10^{-2}$ %/min) |
|---|---|---|---|---|---|---|---|---|---|---|---|---|
| 0 | 19.33 ± 2.85 | 0.99 ± 0.00 | 97.22 ± 0.16 | 4.15 ± 0.29 | 1.86 ± 0.64 | 3.13 ± 1.40 | 10.33 ± 3.93 | 25.29 ± 6.07 | 1.42 ± 0.13 | 28 ± 1.73 | 70.07 ± 6.30 | 4.90 ± 0.26 |
| 5 | 23.33 ± 3.28 | 0.74 ± 0.10 | 72.66 ± 9.84 | 6.10 ± 0.36 | 2.68 ± 0.45 | 2.00 ± 00 | 11.67 ± 1.67 | 16.98 ± 3.65 | 0.88 ± 0.14 | 30.33 ± 5.49 | 53 ± 5.92 | 1.83 ± 0.58 |
| 10 | 37.00 ± 5.13 | 0.51 ± 0.05 | 50.55 ± 5.69 | 7.44 ± 0.40 | 5.82 ± 2.24 | 3.33 ± 0.67 | 23.33 ± 10.14 | 13.04 ± 4.56 | 0.69 ± 0.12 | 44.33 ± 5.36 | 31.68 ± 4.30 | 0.87 ± 0.09 |
| 25 | 99.00 ± 0.00 | 0.24 ± 0.03 | 23.45 ± 2.68 | 8.57 ± 0.21 | N/D | N/D | N/D | N/D | N/D | N/D | N/D | N/D |

We claim:

1. A device for capturing clot contraction comprising:
- a strip;
- at least one reaction chamber housed within the strip sized to allow formation of a platelet-fibrin clot therein;
- a light source positioned to provide about equal illumination to all reaction chambers;
- an aperture between the light source and the at least one reaction chamber to limit stray light;
- a diffuser positioned between the light source and the at least one reaction chamber, the diffuser comprising a translucent material to diffuse the light from the light source; and
- an image capturing device capable of taking digital or digitizable images and of taking time lapse photos over a time interval, positioned at a fixed distance from the strip;
- wherein at least one reaction chamber comprises a reaction medium, an acrylamide plug and a reaction mixture, wherein the reaction medium is comprised of at least two of a plurality of platelets, calcium, fibrinogen, and thrombin or at least two of platelet rich plasma (PRP), calcium, and thrombin.

2. The device of claim 1, wherein the strip comprises an upper strip and a lower strip, the upper strip and the lower strip maintained in a parallel horizontal arrangement with the upper strip comprising an opening to receive passage of the reaction chamber and allow the reaction chamber to rest on the lower strip.

3. The device of claim 1, wherein the at least one reaction chamber comprises all four of platelets, calcium, fibrinogen, and thrombin or all three of PRP, calcium, and thrombin.

4. The device of claim 1, further comprising a test compound.

5. The device of claim 1, wherein the strip is housed in a light impermeable enclosure.

6. The device of claim 1, wherein the image capturing device is positioned at the fixed distance from the strip by an arm operably connected to the strip or a surface underneath the strip.

7. The device of claim 6, wherein the arm is adjustable in length and/or height.

8. The device of claim 1, further comprising an opaque material to control light in the reaction chamber.

9. The device of claim 1, wherein the strip is curved to provide equidistance between each reaction chamber and the image capturing device.

10. The device of claim 1, wherein the strip is linear.

11. The device of claim 1, wherein the one or more reaction chambers are transparent or comprise a transparent window.

12. The device of claim 1, wherein the image capturing device is operably connected to a computer or data processing means.

13. A method for quantifying clot contraction comprising:
- adding a test compound to the device of claim 1;
- capturing a series of images with the image capturing device over a time course;

image processing and defining the edges of the clot side-view profile;

measuring a clot side-view projection area within the at least one reaction chamber within each of the series of images; and correlating the clot side-view cross-sectional area within each of the series of images to the time course to determine lag time, first derivative of the % clot area-time curve, extent of clot contraction (or clot side-view cross-sectional area change), and rates of clot contraction phases.

14. The device of claim 1, wherein the strip is configured to provide an unobscured view of the reaction chamber from a direction perpendicular to a plane of the strip housing the reaction chamber.

* * * * *